US009890355B2

(12) United States Patent
Chang et al.

(10) Patent No.: US 9,890,355 B2
(45) Date of Patent: Feb. 13, 2018

(54) ELECTROPORATION SYSTEMS HAVING A PLURALITY OF HOLLOW MEMBERS

(71) Applicant: LIFE TECHNOLOGIES HOLDINGS PTE. LTD, Chromos (SG)

(72) Inventors: Jun-Keun Chang, Seoul (KR);
Keun-Chang Cho, Seoul (KR);
Chan-Il Chung, Gyeonggi-Do (KR);
Young-Shik Shin, Seoul (KR);
Jeong-Ah Kim, Gyeonggi-Do (KR);
Neon-Cheol Jung, Gyeonggi-Do (KR)

(73) Assignee: Life Technologies Holdings PTE Limited, Singapore (SG)

( * ) Notice: Subject to any disclaimer, the term of this patent is extended or adjusted under 35 U.S.C. 154(b) by 96 days.

(21) Appl. No.: 14/541,833

(22) Filed: Nov. 14, 2014

(65) Prior Publication Data

US 2015/0093813 A1    Apr. 2, 2015

Related U.S. Application Data

(62) Division of application No. 10/560,301, filed as application No. PCT/KR2005/001792 on Jun. 13, 2005, now Pat. No. 8,932,850.

(30) Foreign Application Priority Data

Jun. 12, 2004 (KR) .................. 10-2004-0043312
Nov. 2, 2004 (KR) .................. 10-2004-0088245

(51) Int. Cl.
*C12M 1/34* (2006.01)
*C12M 1/42* (2006.01)
(Continued)

(52) U.S. Cl.
CPC ............. *C12M 35/02* (2013.01); *C12N 13/00* (2013.01); *C12N 15/89* (2013.01)

(58) Field of Classification Search
CPC ......... C12M 35/02; C12N 13/00; C12N 15/89
See application file for complete search history.

(56) References Cited

U.S. PATENT DOCUMENTS 4,099,548 A    7/1978 Sturm et al.
5,007,995 A    4/1991 Takahashi et al.
(Continued)

FOREIGN PATENT DOCUMENTS

EP    0338667    10/1989
JP    63049070    3/1988
(Continued)

OTHER PUBLICATIONS

U.S. Appl. No. 10/560,301, Office action dated Mar. 7, 2011, 9 pgs.
(Continued)

*Primary Examiner* — William H Beisner

(57) ABSTRACT

An electroporation apparatus comprising an elongated hollow member in order to provide a uniform electric field during electroporation, wherein specifically, electroporation is carried out b applying electric pulses through a couple of electrodes from both end parts of the elongated hollow member, after the hollow member is charged with fluid specimen including cells and material which would be injected into the cells.

20 Claims, 31 Drawing Sheets

(51) Int. Cl.
*C12N 13/00* (2006.01)
*C12N 15/89* (2006.01)

(56) References Cited

U.S. PATENT DOCUMENTS

| | | | |
|---|---|---|---|
| 6,074,605 | A | 6/2000 | Meserol et al. |
| 6,241,701 | B1 | 6/2001 | Hofmann |
| 6,287,776 | B1 | 9/2001 | Hefti |
| 6,293,749 | B1 | 9/2001 | Raaijmakers et al. |
| 6,352,853 | B1 | 3/2002 | King et al. |
| 6,356,173 | B1 | 3/2002 | Nagata et al. |
| 6,627,421 | B1 | 9/2003 | Unger et al. |
| 6,628,382 | B2 | 9/2003 | Robertson |
| 6,677,114 | B1 * | 1/2004 | Schneider ............ B65G 59/066 435/4 |
| 6,897,069 | B1 | 5/2005 | Jarvis et al. |
| 6,936,462 | B1 | 8/2005 | Owen et al. |
| 7,384,781 | B2 | 6/2008 | Moyle et al. |
| 7,393,681 | B2 | 7/2008 | Jarvis et al. |
| 7,456,012 | B2 | 11/2008 | Ryttsén et al. |
| 7,678,564 | B2 | 3/2010 | Muller-Hartmann et al. |
| 8,017,399 | B2 | 9/2011 | Jarvis et al. |
| 8,101,401 | B2 | 1/2012 | Muller-Hartmann et al. |
| 2003/0009148 | A1 | 1/2003 | Hayakawa |
| 2003/0022153 | A1 * | 1/2003 | Kirk ...................... B01L 3/5085 435/4 |
| 2003/0070923 | A1 | 4/2003 | Schroeder et al. |
| 2005/0164161 | A1 | 7/2005 | Augustine et al. |
| 2007/0275454 | A1 | 11/2007 | Chang et al. |
| 2008/0064511 | A1 | 3/2008 | Brace et al. |
| 2008/0213854 | A1 | 9/2008 | Wirth et al. |
| 2010/0196998 | A1 | 8/2010 | Jarvis et al. |
| 2011/0263005 | A1 | 10/2011 | Chang et al. |

FOREIGN PATENT DOCUMENTS

| | | |
|---|---|---|
| JP | 11290058 | 10/1999 |
| JP | 2002504232 | 2/2002 |
| JP | 2007167006 | 7/2007 |
| JP | 2008502356 | 1/2008 |
| JP | 2008/051169 | 5/2008 |
| KR | 10-1084528 | 11/2011 |
| WO | WO-1998/058251 | 12/1998 |
| WO | 1999/024110 | 5/1999 |
| WO | 2000/063408 | 10/2000 |
| WO | 2002/033066 | 4/2002 |
| WO | 2003/057819 | 7/2003 |
| WO | 2004/031353 | 4/2004 |
| WO | 2005/123931 | 12/2005 |
| WO | 2006/001614 | 1/2006 |
| WO | WO-2009/129327 | 10/2009 |

OTHER PUBLICATIONS

U.S. Appl. No. 10/560,301, Office Action dated Sep. 22, 2010, 5 pgs.
CA 2,570,557, Notice of Allowance dated Jun. 21, 2010.
CA 2,570,557, Office Action dated May 7, 2009.
CA 2,570,557, Response Office Action filed Nov. 6, 2009, 20.
CN 200580018428.8, Office action dated Mar. 11, 2010.
CN 200580018428.8, Response to Office action filed May 26, 2010.
JP 2007527027, Response to Office Action filed on Mar. 12, 2010.
JP 2007-527027, Office Action dated Oct. 13, 2009.
EP 5750475.5, Office Action dated Aug. 17, 2010.
EP 5750475.5, Office Action dated Feb. 15, 2010.
EP 5750475.5, Response to Office Action filed on Dec. 17, 2010, 3 pgs.
EP 57504755, Response to Office Action filed on Jul. 5, 2010, 3 pgs.
Dong, et al., "Monitoring diclofenac sodium in single human erythrocytes introduced by electroporation using capillary zone electrophoresis with electrochemical detection", *Electrophoresis*, vol. 22, No. 13, Aug. 2001, 2786-2792.
Hu, et al., "Inhibition of Retroviral Pathogenesis by RNA Interference", *Current Biology*, vol. 12, Issue 15, Aug. 6, 2002, 1301-1311.
Lin, et al., "Electroporation microchips for continuous gene transfection", *Sensors and Actuators B*, vol. 79, 2001, 137-143.
Nolkrantz, et al., "Electroporation of Single Cells and Tissues with an Electrolyte-filled Capillary", *Analytical Chemistry*, vol. 73, Issue 18,, Sep. 15, 2001, 4469-4477.
Osumi, et al., "Gene Transfer into Cultured Mammalian Embyos by Electroporation", *Methods*, vol. 24, 2001, 35-42.
Speyer, et al., "A Simple and Effective Electroporation Apparatus", *Biotechniques*, vol. 8, No. 1, Jan. 1990, 28-30.
Speyer, "Multi-Sample Electroporation", *BioTechniques*, vol. 8, No. 5, May 1990, 508.

* cited by examiner (a)

(b)

(a)
(b)
(c)

ELECTROPORATION SYSTEMS HAVING A PLURALITY OF HOLLOW MEMBERS

CROSS-REFERENCE TO RELATED APPLICATIONS

This application is a divisional of U.S. application Ser. no. 10/560,301 filed May 30, 2007, now U.S. Pat. No. 8,932,850, which was a 371 national phase of International application no. PCT/KR2005/001792 filed Jun. 13, 2005, and which claimed priority to KR application no. 10-2004-0088245 filed Nov. 2, 2004 and KR application no. 10-2004-0043312 filed Jun. 12, 2004, which disclosures are herein incorporated by reference in their entirety.

FIELD OF THE INVENTION

The present invention relates to an electroporation apparatus having an elongated hollow member and an electroporating method, whereby an electric pulse or electric pulses are applied to a specimen including cells, and cell membranes are electrically perforated to thereby enable to introduce a foreign material into the cell.

DESCRIPTION OF THE PRIOR ART

In general, an electroporation is a kind of technique for introducing macromolecules into cells by electric pulses which cannot penetrate cell membrane. The electroporation is a widely used and strongly recommended method directly applicable to cell experiment and gene therapy. If a high electric field is applied, cell membranes temporarily become porous to show permeability to foreign materials.

The said electropermeabilization depends on various factors such as pulse width, pulse duration, number of pulses and other experimental conditions. Many researchers have performed various studies relative to the above-mentioned parameters in order to understand the mechanism of the electroporation and to promote the effect of transfection. Intensity of electric field is reported to work as a decisive parameter for permeating the membrane and controlling the scope of cell area where transmission occurs. Of course, studies on other parameters have progressed as well. However, little is known about the response to cell relative to the electric pulse and mechanism of transfection. Due to scanty and poor theory on the electroporation, visualization of the electroporation has surfaced as one of the important matters.

Referring to FIG. 1, in order to apply an electric field to compound of cell suspension and gene, a cuvette equipped with two parallel electrode plates (200) is usually used. If a high electric field is applied to the electrode plates (200), it is possible to introduce a gene into the cell. Aluminum electrodes for disposable cuvette are used.

However, $Al^{3+}$ ions dissolved from the aluminum electrodes are reported to have a bad influence on the cells. Furthermore, if aluminum electrodes are used, the intensity of electric field can vary due to drop in electric voltage between oxide layers on the electrodes. Therefore, it is preferred to use platinum or gold electrodes. However, electrodes of these materials are very expensive so that it is difficult in reality to use electrodes of these materials as electrodes of cuvette disposed after one or few times of use. FIG. 2 is a photograph of a square wave electroporation apparatus (ECM 830, BTX, USA) as shown for a conventional electroporation apparatus.

However, this illustrated electroporation apparatus has the following disadvantages. First of all, cuvette is too expensive because of the aluminum blocks used as electrodes. The manufacturers of electroporation apparatuses therefore recommend that cuvette be used once, however, many users conduct experiments repeatedly several times, so there is a high possibility of occurrences of experimental errors. Secondly, because the electrode material (Al) is reactive in solution, and the overpotential relative to hydrogen generation is low, the said electroporation easily creates air bubbles due to decomposition of water on the surfaces of the electrodes. Thirdly, the generated ion ($Al^{3+}$) has a bad effect on the cells. Fourthly, surface resistance is markedly increased due to generated oxide layer ($Al_2O_3$). Fifthly, the electric field is not even. This is because a large quantity of current flows through corners of the electrodes, thereby creating a distortion to the electric field. Sixthly, the specimen becomes voluminous, which makes it inappropriate for a small quantity of cells to be analyzed. Seventhly, several steps of sample handling are required to fill in and out the cuvette with specimen. Eighthly, high throughput electroporation is not possible because it is not easy to integrate cuvette handling process into the robotic systems. Ninthly, the decomposition of water at the electrode surfaces induces severe pH variation that is harmful to cells. The needs have arisen to develop a new electroporation apparatus to address these disadvantages.

In order to address the above-mentioned disadvantages, inventors of the present invention have used an electroporation apparatus having an elongated hollow specimen-stuffing member of non-conductive material, wherein both distal ends of the specimen-stuffing member is applied with electric pulse so that an electricity can flow through a specimen stuffed in the specimen-stuffing member. The inventors have used this eletroporator and carried out the electroporation, and have compared a biological result thereof with the conventional electroporation method for completion of the invention.

DETAILED DESCRIPTION OF THE INVENTION

Technical Subject

The object of the present invention is to provide an electroporating method using an elongated hollow specimen-stuffing member.

Another object is to provide an electroporation apparatus.

Still another object is to provide an electroporation system.

Technical Solution

The present invention relates to an electroporating method for introducing foreign materials into cells by applying an electric field to a specimen to thereby enable to electroporate cell membranes. More particularly, the present invention relates to an electroporating method, an electroporation apparatus, and an electroporation system, wherein an elongated hollow specimen-stuffing member of non-conductive material in which the electroporation is carried out is used, and an electric pulse is applied through electrodes from both distal ends thereof so that the electroporation can be effectively implemented within the specimen-stuffing member.

In a preferred embodiment of the present invention, an electroporation apparatus is provided, comprising hollow specimen-stuffing member, a reservoir and a pressure maintaining means connected to one distal end of the specimen-stuffing member to fluidly communicate with the distal end and to provide an appropriate pressure for maintaining the specimen in the specimen-stuffing member so that the specimen-stuffing member is supplied with a specimen. The electroporation apparatus according to the present invention is constructed in such a manner that a distal end of the specimen-stuffing member and the pressure maintaining means may be connected directly or via a connector (for example, T-shaped connector or Y-shaped connector).

If the pressure maintaining means is connected to the specimen-stuffing member via a connector, the connector is laterally disposed with an electrode insertion unit for inserting an electrode, and the electrode inserted into electrode insertion unit contacts a specimen if the specimen-stuffing member is stuffed therein with the specimen. The pressure maintaining means at the electroporation apparatus according to the present invention may be a pump, a syringe or a pipette. In implementing the electroporation using the electroporation apparatus according to the present invention, the specimen including cells is first stuffed into the specimen-stuffing member by using the pressure maintaining means. Electrolytic solution is infused into a reservoir where an electrode has been inserted, and a distal end of the hollow specimen-stuffing member of the electroporation apparatus is so connected as to allow the electrolytic solution of the reservoir to be fluidly communicated. In addition, an electric pulse is applied to the electrode at the reservoir and the electrode inserted into the connector, thereby enabling to electroporate cells out of specimen stuffed in the specimen-stuffing member.

In another preferred embodiment of the present invention, the electroporation apparatus including a hollow specimen-stuffing member, a reservoir, a reservoir holder and a pressure maintaining means according to the present invention is constructed in such a manner that the pressure maintaining means is a pipette; the pipette is disposed at a body thereof with a conductive contact; and a movable electrode disposed inside the specimen-stuffing member cooperates with a piston and is easily detached and attached. The movable electrode serves to function as a plunger for infusing the specimen into the specimen-stuffing member and simultaneously as an electrode for electrically connecting the specimen via a conductive contact. A pipette tip is comprised of a specimen-stuffing member and a movable electrode which reciprocates therein, and is directly connected to a shaft for mounting the pipette tip. If a piston of the pipette is worked to allow the movable electrode to move horizontally inside the pipette tip and to allow the specimen to be infused into the specimen-stuffing member, the specimen contacts the movable electrode and is electrically connected to the conductive contact of a pipette body. In the preferred embodiment, the other electrode is disposed at a floor surface of the reservoir where the electrode contacts the stored electrolytic solution or the specimen and is attached and detached to a cylinder-shaped reservoir holder inner pipe. A reservoir holder is disposed thereon with fixing units for fixing a pipette and a reservoir and an electrode terminal connected via the inner pipe to the electrode of the reservoir. The reservoir holder is so constructed as to be separated as a body and a lid, or may be constructed in an integral form.

As mentioned earlier, the present invention provides an electroporation system comprising an electroporation apparatus and an electric pulse generator.

In the electroporation system according to the present invention, if an electric pulse is applied to one electrode contacting electrolytic solution or a specimen stored in a reservoir and the other electrode inserted into a connector or cooperating with a piston, cells contained in a specimen stuffed in a specimen-stuffing member can be electroporated.

Furthermore, the hollow specimen-stuffing member according to the present invention can be provided in channel structure. A channel is integrally provided by coupling upper and lower plates, wherein both distal ends of the channel are connected to a pair of well shaped reservoirs in a fluid communicative manner. If a specimen is infused into one of the wells and stuffed in the channel by capillary action, water head pressure or pumping action, and an overdosed specimen is filled in other well, an electroporation into cells within the channel can be carried out in such a manner that a pair of electrodes are inserted in the respective wells to thereby apply an electric field into the channel.

Preferably, the electroporating method according to the present invention comprises the steps of: stuffing an interior of a specimen-stuffing member with a specimen using a pressure maintaining means, capillary action or water head pressure; connecting both distal ends of the specimen-stuffing member of the electroporating device to specimens or electrolytic solution stored in reservoirs via fluid communicative manner; and inserting electrodes into each reservoir and applying an electric pulse to the inserted electrodes to electroporate cells in the specimen stuffed in the specimen-stuffing member. If the specimen is too small, it is preferred that a reservoir containing the specimen should be replaced by a reservoir containing only the electrolytic solution before the electrodes are inserted into the reservoir and the specimen is electrically connected to the electrodes.

Preferably, the specimen-stuffing member and the reservoir are non-conductive materials such that transparent plastic or glass is used. Therefore, Polydimthylsiloxane (PDMS), Polymethylmethacrylate (PMMA), Polycarbonate (PC), Cyclicolefin Copolymer (COC), Polystyrene (PS), Polyethylene (PE), Copolyster Thermoplastic Elastomer (TPC), Polyimide, Polypropylene, Silicon, Glass, Quartz or the like is used as material for the specimen-stuffing member and the reservoir but it is not limited thereto. Furthermore, the electroporating device having a specimen-stuffing member of micro channels thus described can be easily integrated with other systems for mixture, filtering, polymerase chain reaction or capillary electrophoresis.

The exemplary plastic materials have an excellent merit as materials for the hollow specimen-stuffing member and reservoir. By using those materials, it is easy to manufacture micro channel device according to the present invention. Furthermore, these materials are reasonable in cost, transparent and appropriate for a living body. If a transparent plastic material is used, it is possible to observe in real time a process of material being absorbed into cells. As a result, a process of transferring a gene into a living cell can be visually observed.

Furthermore, another electroporating method according to the present invention comprises the steps of: filling an interior of a specimen-stuffing member with specimens using a pressure maintaining means such as a syringe or a pump; connecting a distal end of the specimen-stuffing member of the electroporating device to a specimen or electrolytic solution via fluid communicative manner; and electroporating cells in the specimens filled in the specimen-stuffing member by inserting an electrode into a reservoir and inserting the other electrode into an electrode insertion part of a connector for connecting the pressure maintaining means to the specimen-stuffing member, and applying an electric pulse to the inserted electrodes. If the specimen is too small, it is preferred that a reservoir containing the specimen should be replaced by a reservoir containing only the electrolytic solution before the reservoir is inserted by the electrodes and is made to contact the specimen.

Still further electroporating method according to the present invention comprises the steps of: filling an interior of a specimen-stuffing member with specimens using a pipette-type pressure maintaining means; filling the reservoir with electrolytic solution and inserting it into a reservoir holder; inserting the pipette-type pressure maintaining means into the reservoir holder and fixing it by fixing unit and connecting a distal end of the specimen-stuffing member to the specimen or electrolytic solution via fluid communicative manner; and electroporating cells in the specimen filled in the specimen-stuffing member by applying an electric pulse to the electrode equipped at the reservoir and a movable electrode in the pipette. If the specimen is too small, it is preferred that a reservoir containing the specimen should be replaced by a reservoir containing only the electrolytic solution before the electrodes are inserted into the reservoir and are made to contact the specimen.

Furthermore, the present invention can continuously perform the electroporation by adjusting the supply maintenance and removal of specimen to be continuously implemented inside the hollow specimen-stuffing member.

In the electroporation apparatus, electroporation system or electroporating method according to the present invention, an electrode may be made of any conductive material, and it is preferred that a platinum electrode, a gold electrode, a silver electrode, a copper electrode or plastic plated with the aforementioned metals is used. Furthermore, the pressure maintaining means may be a pump, a syringe or a pipette. The hollow specimen-stuffing member is preferred to be a capillary, a tubing or a channel. In case of a channel, it is preferred to be a micro channel. Particularly, the specimen-stuffing member should have a ratio (R, cm$^{-1}$) of a longitudinal length (L, cm) to horizontal cross-sectional area (A, cm$^2$) of the specimen-stuffing member in the range of 50 to 10,000.

Information with regard to the electroporating state of cells can be electrically measured by easily measuring a current flowing through the specimen-stuffing member. The electroporation apparatus according to the present invention can be effectively used for electroporation which is a first step of DNA transmission, and can contribute to study of mechanism of electroporation. Furthermore, the electroporation apparatus can be miniaturized in gene manipulation.

Now, an electroporation apparatus, an electroporation system and an electroporation method according to the present invention will be described in detail with reference to the accompanying drawings. Throughout the drawings, explanation about like or equivalent portions or parts are not repeated in order to avoid redundancy. While the present invention has been described in connection with certain preferred embodiments, it is to be understood that the subject matter encompassed by way of the present invention is not to be limited to those specific embodiments. On the contrary, it is intended for the subject matter of the present invention to include all the alternatives, modifications, and equivalents as can be included within the spirit and scope of the following claims. Documents cited by the present invention are incorporated as references in the present invention.

Figure 3:
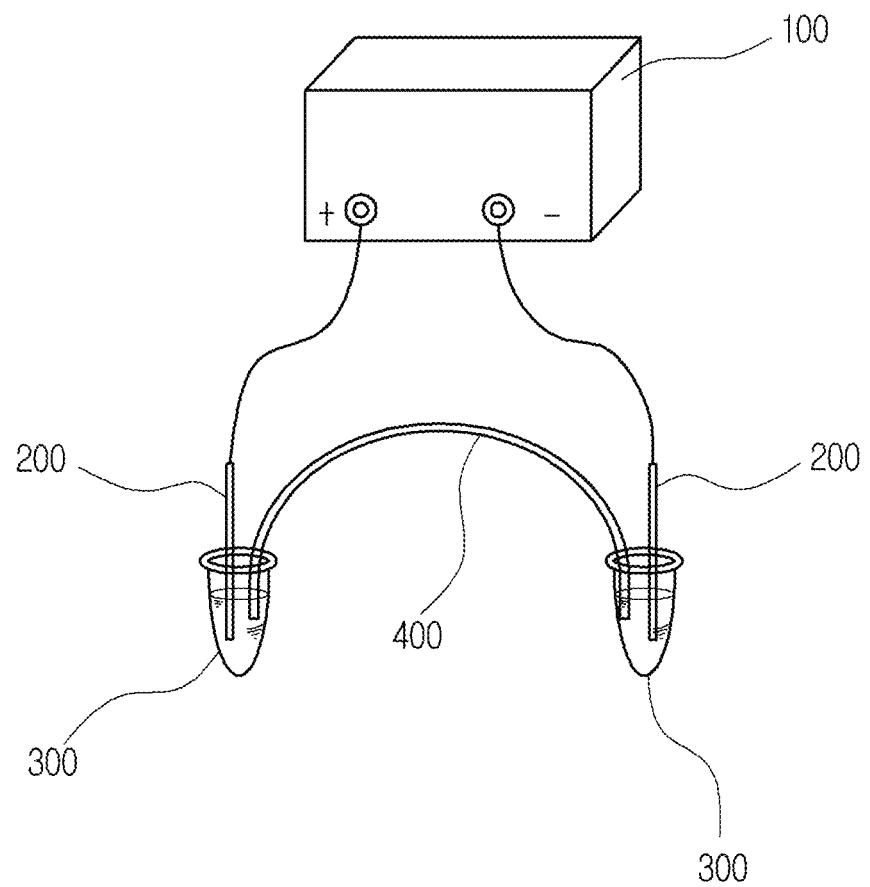
FIG. 3 illustrates a structure of an embodiment of an electroporation system according to the present invention.

FIG. 3 illustrates a structure of an embodiment of an electroporation system according to the present invention. The electroporation system comprises: a pulse generator (100) for generating an electric pulse; a pair of reservoirs (300) for storing specimens; and a specimen-stuffing member (400) such as a capillary or a tubing stuffed therein with specimens. The pair of reservoirs (300) are so connected that fluid can be intercommunicated by the specimen-stuffing member (400). The pair of reservoirs (300) are respectively inserted by electrodes (200) for electric connection with the pulse generator (100). Electroporation of cells in a specimen stuffed in the specimen-stuffing member (400) can be conducted by applying an electric field to the electrodes (200). At this time, the specimen-stuffing member (400) may be opened at both distal ends or at any one distal end only. In other words, as long as it is appropriate for the specimen-stuffing member (400) to be filled with specimens and for both distal ends thereof to be applied with electric voltages, it suffices that any part of the specimen-stuffing member may be opened.

Figure 4:
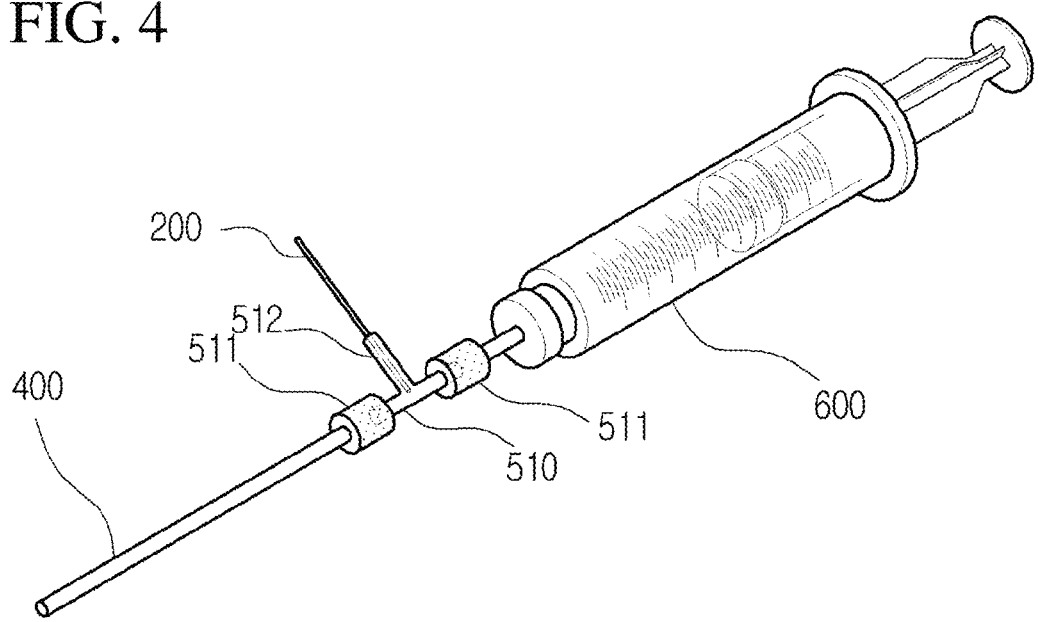
FIG. 4 illustrates a structure of an embodiment of an electroporation system according to the present invention.

FIG. 4 illustrates a structure of an embodiment of an electroporation system according to the present invention. The electroporation system comprises: a singular reservoir (not shown); a hollow specimen-stuffing member (400) such as a capillary or a tubing; and a syringe (600) of a pressure maintaining means connected to a distal end of the specimen-stuffing member (400) for maintaining a proper pressure so that the specimen-stuffing member can be filled with specimens in an interior thereof. In the electroporation system in FIG. 4, the distal end of the specimen-stuffing member (400) and the pressure maintaining means (600) are connected by a T-shaped connector (510). The T-shaped connector (510) is formed with an electrode insertion part (512) into which an electrode (200) is inserted for applying an electric pulse. The specimen-stuffing member (400) is filled therein with specimens, and the electrode (200) contacts the specimen. An adapter (511) connects a distal end of the specimen-stuffing member (400) to the connector (510), and connects the connector (510) to the pressure maintaining means (600).

Figure 5:
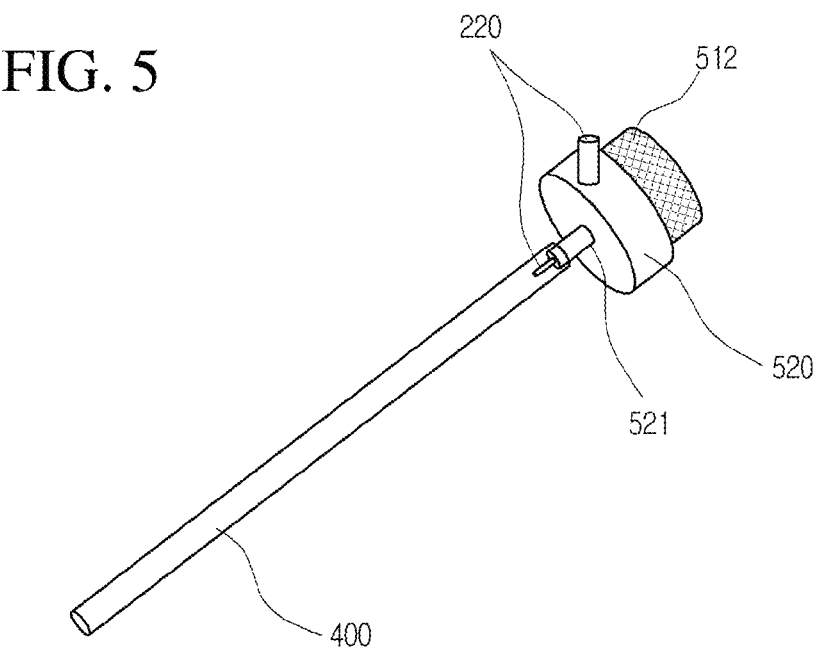
FIG. 5 illustrates a connected state between a disc-shaped connector and a capillary in an electroporation apparatus according to the present invention.

FIG. 5 illustrates a connected state between a disc-shaped connector (520) and a specimen-stuffing member (400), wherein the disc-shaped connector (520) is used to connect the specimen-stuffing member and a pressure maintaining means in an electroporation apparatus according to the present invention. The disc-shaped connector (520) in FIG. 5 is formed therein with a hole (521) through which a specimen can pass, and the electrode insertion part (512) is formed at a disc lateral surface. An L-shaped electrode (220) is inserted into the electrode insertion part (512) such that if the specimen-stuffing member (400) is filled therein with specimens, the electrode contacts the specimen.

Figure 6:
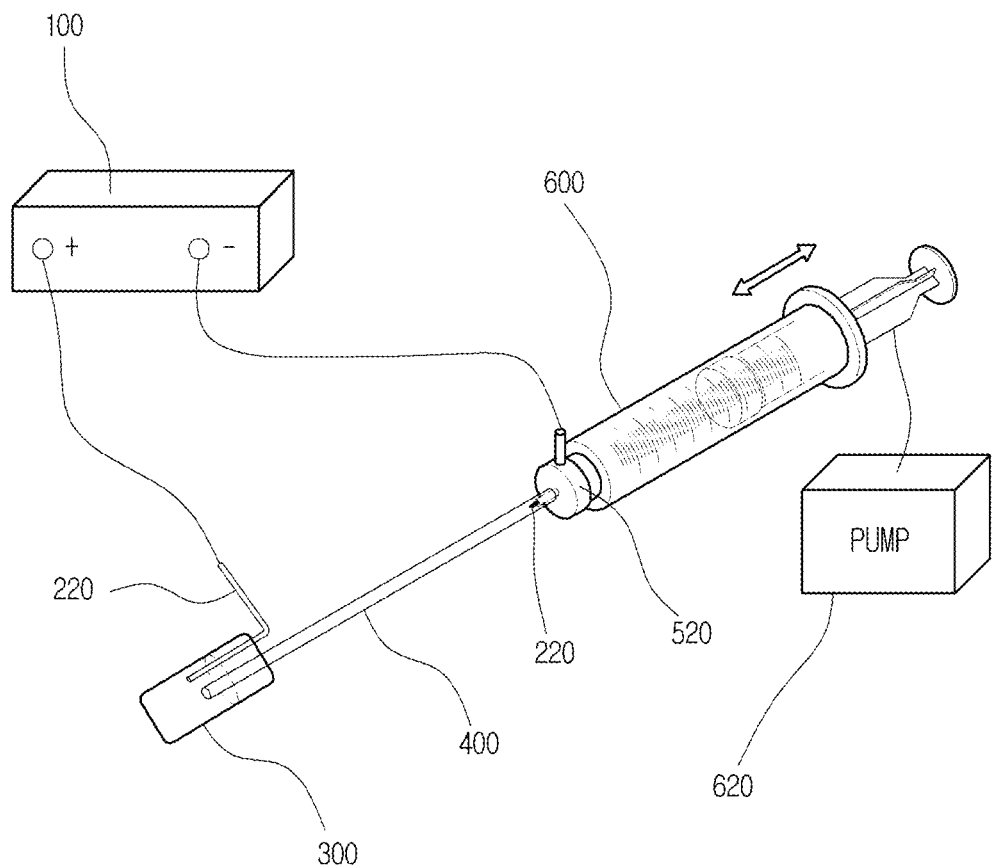
FIG. 6 illustrates an embodiment of an electroporation system according to the present invention.

FIG. 6 illustrates an embodiment of an electroporation system according to the present invention. The electroporation system comprises: a reservoir (300); an electroporation apparatus as shown in FIG. 4; and a pulse generator (100) for generating an electric pulse. A specimen including cells or electrolytic solution is stored in the reservoir (300), and an electrode (200) is inserted into the reservoir (300) to contact the specimen. Furthermore, connection is made in such a manner that a distal end of the specimen-stuffing member (400) can fluidly communicate with the specimen of the reservoir. In implementing the electroporation, a syringe (600) operated by a pump (620) is used as a pressure maintaining means to fill the interior of the specimen-stuffing member (400) with the specimens. At this time, the reservoir in which the specimen is filled may be replaced by a reservoir in which electrolytic solution is filled after the specimen-stuffing member (400) is filled with specimens. Cells in a specimen filled in the specimen-stuffing member (400) can be electropolated by applying an electric pulse between the electrode (200) contacting the specimen or the electrolytic solution stored in the reservoir (400) and the electrode inserted into the connector (520).

Figure 7:
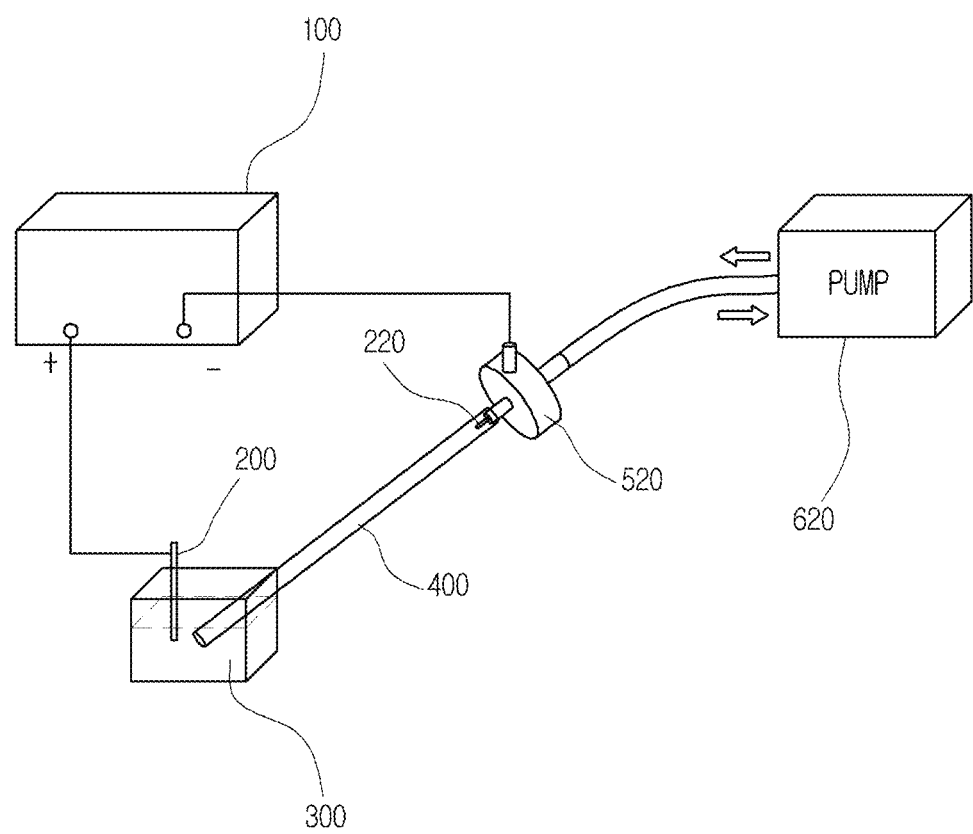
FIG. 7 illustrates another embodiment of an electroporation system according to the present invention.

FIG. 7 illustrates another embodiment of an electroporation system according to the present invention, wherein a pump (620) is used as a pressure maintaining means so connected to fluidly communicate with a distal end of the specimen-stuffing member. Therefore, the specimen-stuffing member (400) is connected to the pump (620) via the connector (520).

Figure 8:
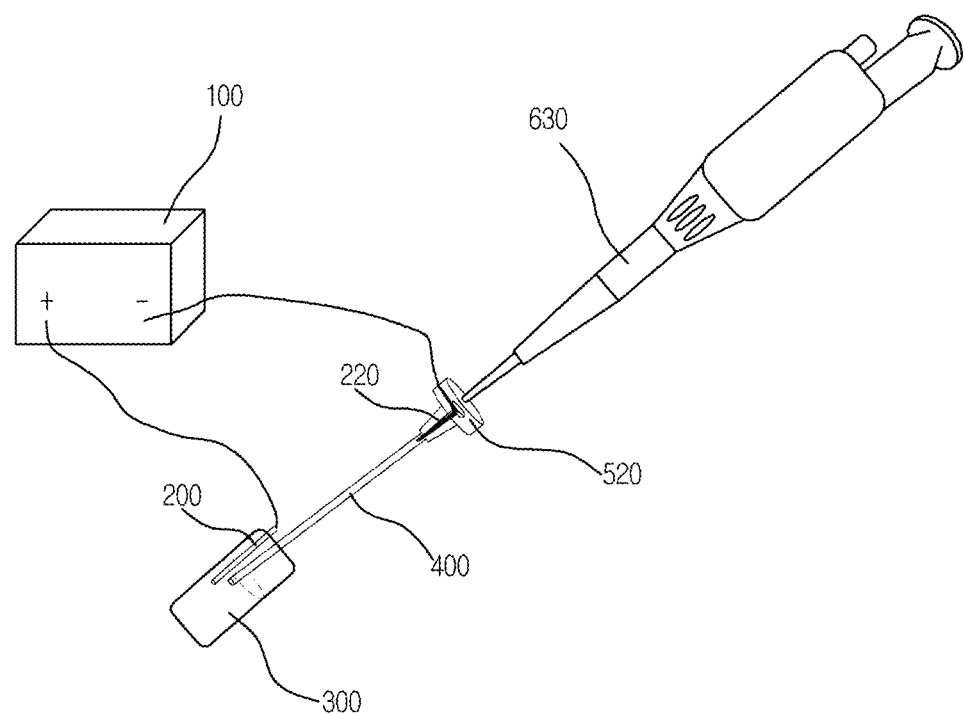
FIG. 8 illustrates still another embodiment of an electroporation system according to the present invention.

FIG. 8 illustrates still another embodiment of an electroporation system according to the present invention, wherein a pipette (630) is used as a pressure maintaining means for fluidly communicating with the specimen-stuffing member. In this figure, the specimen-stuffing member (400) is connected to the pipette (630) via the connector (520).

Figure 9:
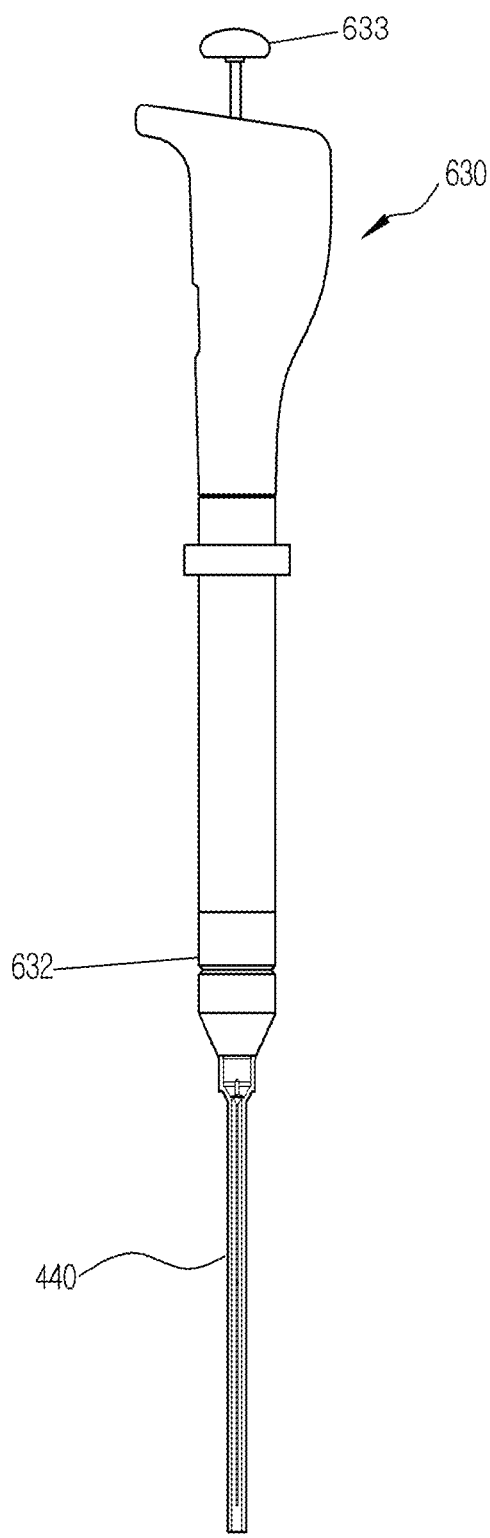
FIG. 9 illustrates a structure of a pipette used for an electroporation apparatus according to the present invention.
Figure 10:
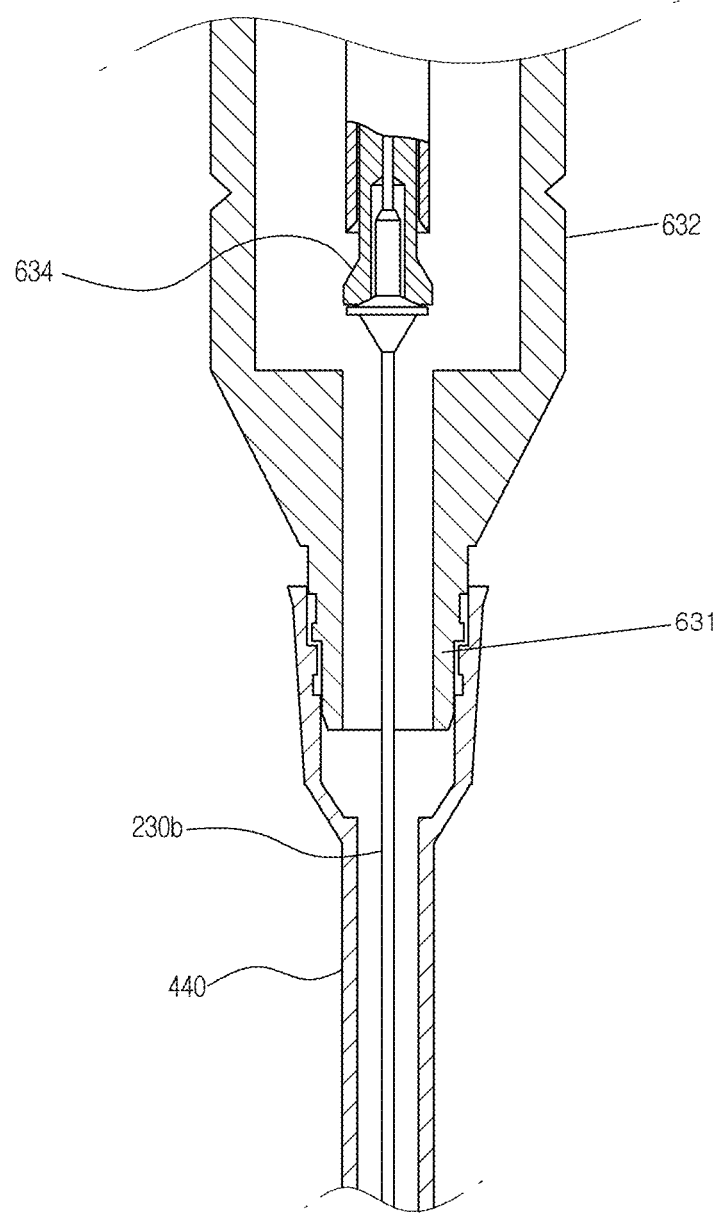
FIG. 10 illustrates a partially enlarged view of the pipette of FIG. 9.
Figure 11:
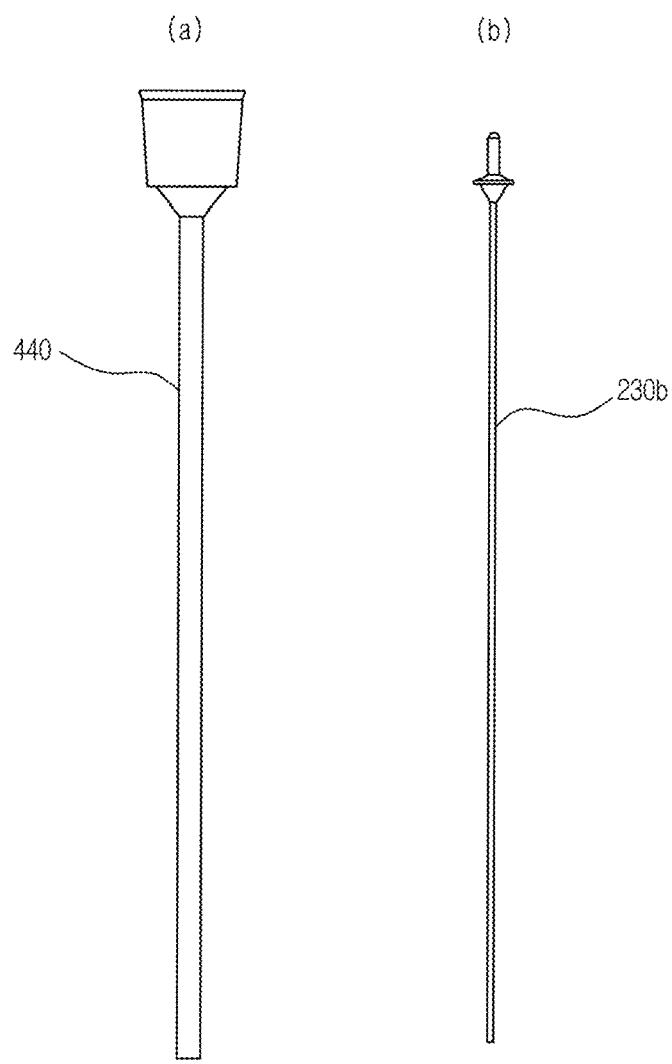
FIGS. 11(a) and (b) illustrate a specimen-stuffing member and a movable electrode used for the pipette of FIG. 9.

FIG. 9 illustrates a structure of a pipette used for an electroporation apparatus according to the present invention, wherein the pipette (630) is used as a pressure maintaining means for fluidly communicating with the specimen-stuffing member. FIG. 10 illustrates a partially enlarged view of the pipette (630) connected to a movable electrode (230b) and a specimen-stuffing member (440). The specimen-stuffing member (440) is directly connected to a pipette tip mounting shaft (631). The pipette (630) used as a pressure maintaining means is disposed at a body thereof with a conductive contact (632), and a movable electrode (230b) is inserted into the specimen-stuffing member and mounted in the pipette so as to communicate with a piston (634) in the pepette and to reciprocate in the specimen-stuffing member. FIGS. 11(a) and (b) illustrate a specimen-stuffing member (440) and a movable electrode (230b) used for the pipette.

Figure 12:
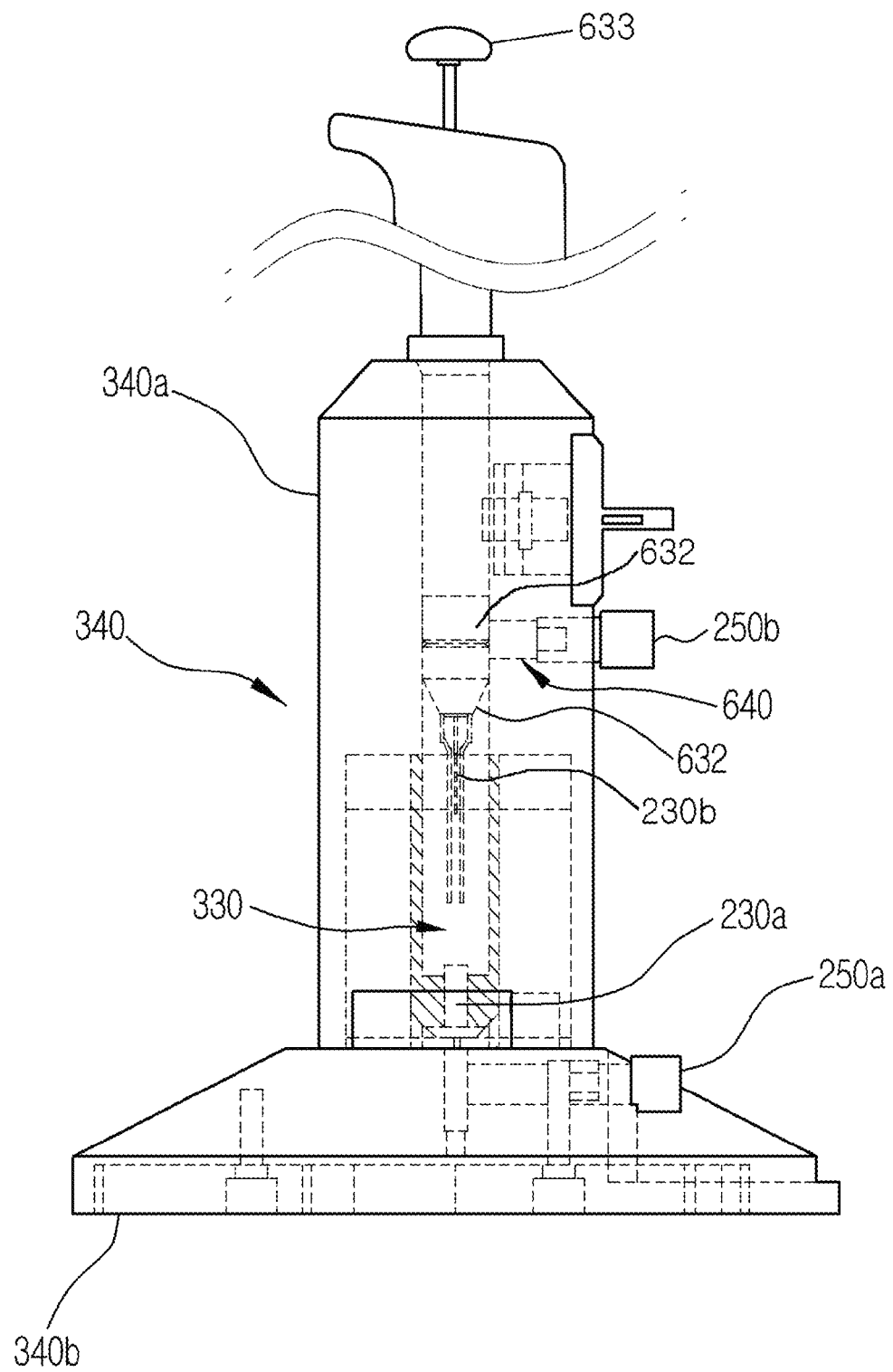
FIG. 12 illustrates a structure of a reservoir and a reservoir holder used for the electroporation apparatus according to the present invention.
Figure 13:
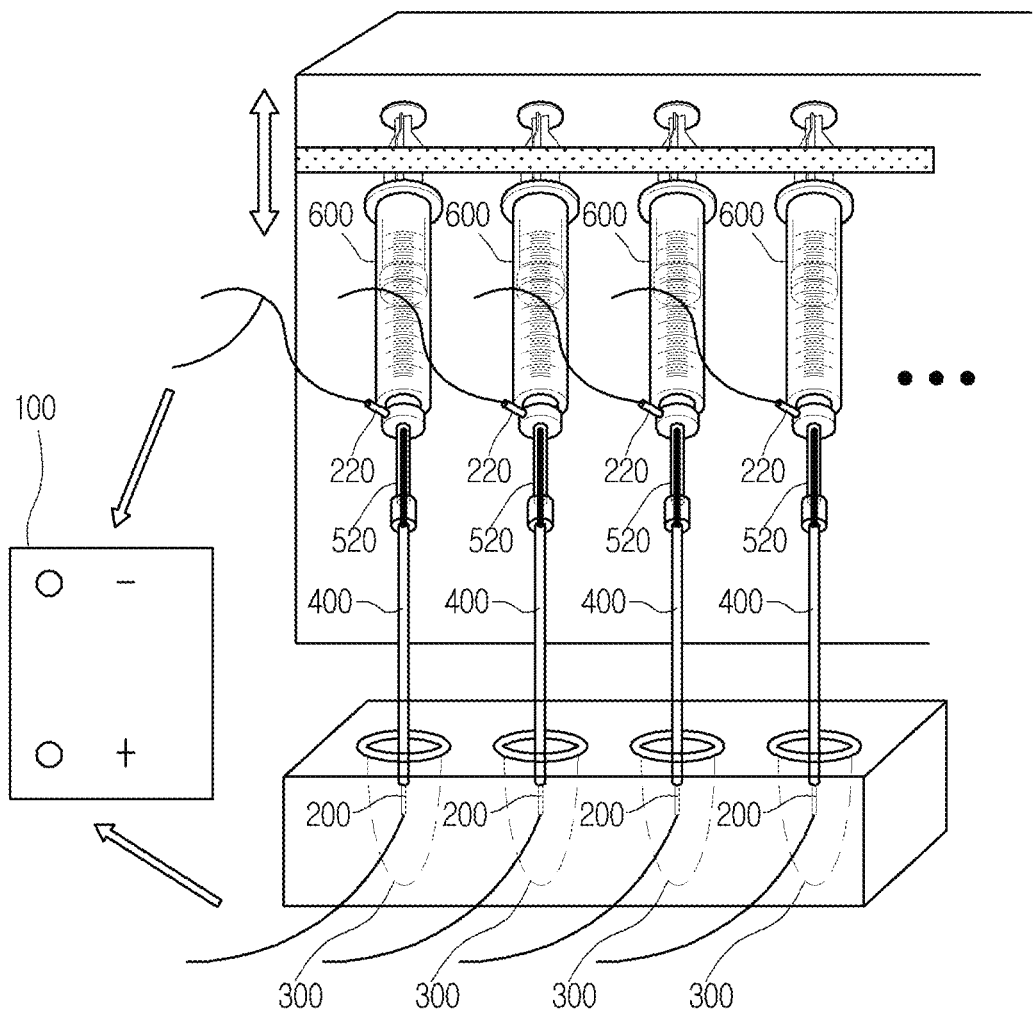
FIG. 13 illustrates an embodiment of an electroporation system according to the present invention.

FIG. 12 illustrates a structure of a reservoir (330) and a reservoir holder (340) used for the electroporation apparatus according to the present invention. The reservoir holder (340) is formed at an upper inner pipe wall with a pipette fixing unit (640) for fixing the pipette, and is also disposed with an electrode terminal (250b) for electrically connecting to the fixing unit (640) and the other electrode terminal (250a) formed at a floor thereof. The reservoir is mounted thereunder with an electrode (230a) for contacting the electrolytic solution or specimen. If the pipette (630) is fixed at the pipette fixing unit (640) of the reservoir holder, the movable electrode (230b), the pipette contact (632) and the pipette fixing unit (640) are electrically connected. In conducting the electroporation, the specimen is picked by a pipette and stuffed in the specimen-stuffing member (440), the reservoir (330) filled with electrolytic solution is inserted into an inner pipe of the reservoir holder (340), the pipette is fixedly inserted into the pipette fixing unit (640) to allow a distal end of the pipette to fluidly communicate with the electrolytic solution of the reservoir, and electric pulse is applied to the two electrodes (230a, 230b) via the electrode terminals (250a, 250b) of the reservoir holder (340) to enable to electroporate the cell in the specimen-stuffing member. After the electroporation, the pipette is separated from the reservoir and the reservoir holder, and a pipette press button (633) is depressed to enable to easily retrieve the electroporated cell. The reservoir holder (340) may be so manufactured as to be separable between an upper lid (340a) and a body (340b) (see FIG. 12), or may be integrally manufactured. The specimen-stuffing member is detachably connected to the pipette tip mounting shaft (631) such that it may be disposably manufactured (see FIG. 10). Furthermore, an automatic electroporation system can be provided using the said electroporation apparatus and the electric pulse generator. FIG. 13 illustrates another embodiment of an electroporation system according to the present invention in which one or more electroporation apparatuses each including a specimen-stuffing member connected to a syringe-type pressure maintaining means are arranged in parallel.

Figure 14:
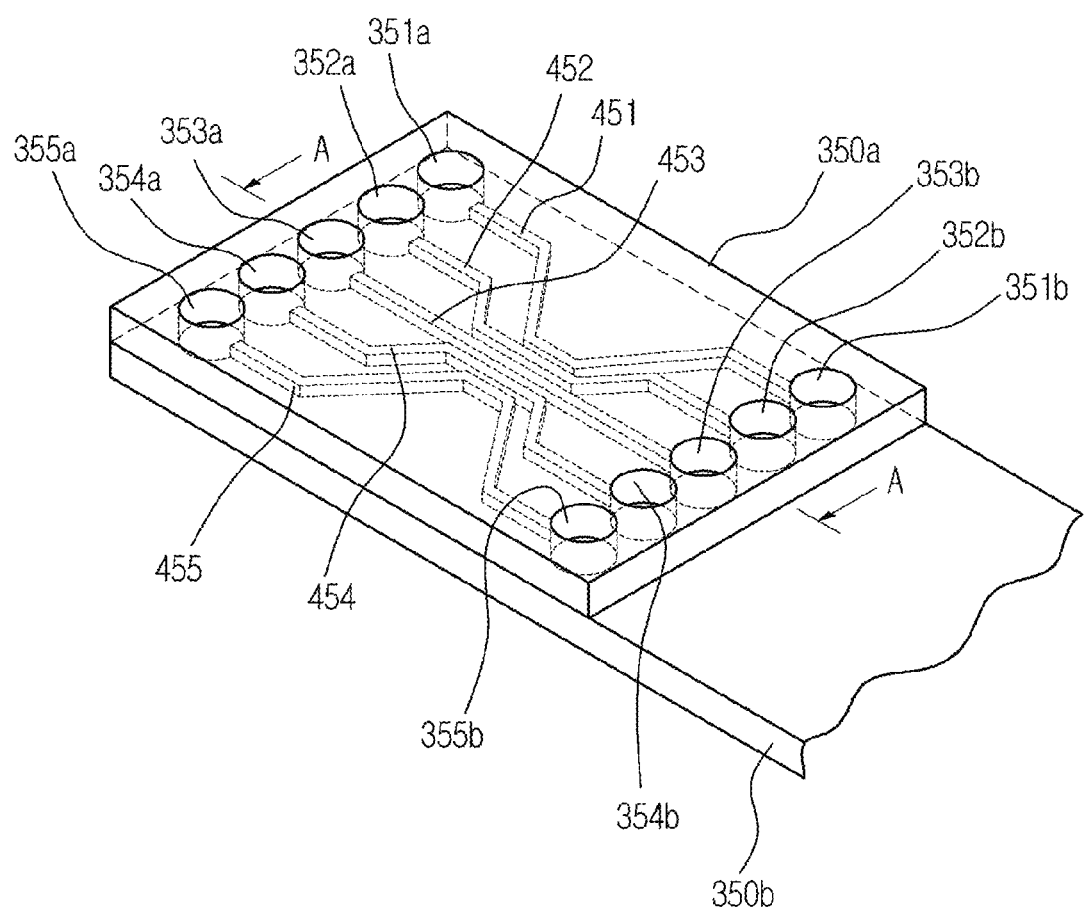
FIG. 14 is a perspective view of an electroporation apparatus having a channel structure according to the present invention.
Figure 15:
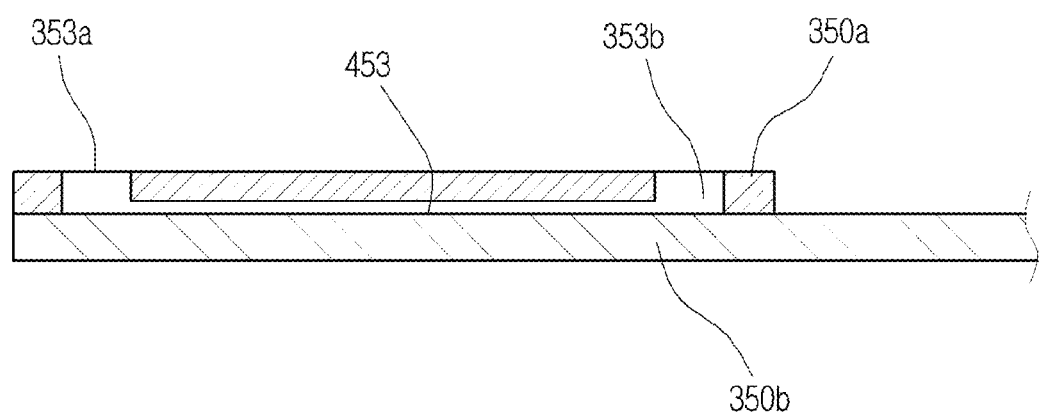
FIG. 15 is a cross-sectional view of an electroporation apparatus of FIG. 14.

FIG. 14 is a perspective view of an electroporation apparatus having a micro channel structured specimen-stuffing member and a well-shaped reservoir according to the present invention. The electroporation apparatus includes a substrate comprised of an upper plate (350a) and a lower plate (350b) on which a micro channel hollow specimen-stuffing member and a pair of wells so connected to fluidly communicate with both distal ends of the specimen-stuffing member are disposed. FIG. 15 is a cross-sectional view taken along line A-A' of FIG. 14. The electroporation apparatus is formed at both sides thereof with one or more pairs of wells (351a~355a, 351b~355b) for inserting electrodes of the pulse generator so that a specimen including cells can be applied with electric pulse, wherein micro channels (451~455) are formed to connect the corresponding wells (351a-351b, 352a-352b, 353a-353b, 354a-354b, 355a-355b). The cell membrane can be electrically perforated and foreign materials can be introduced into the cell by inserting electrodes into the wells and applying the electric pulse. In the aforementioned electroporation apparatus, each channel length of the channels is different. Therefore, even if the same voltage is applied to the electrodes of the pulse generator, the intensity of electric field at each channel is different.

The intensity of the electric field can be obtained by the following Equation 1.

$$E = V/L \quad (1)$$

wherein,
E is the applied intensity of the electric field,
V is the voltage difference between both ends of the electrodes, and
L is the channel length.

As a result, even if the same voltage is applied to both ends of the micro channel, mutually different electric fields can be obtained because the channel length varies.

The electroporation apparatus having the micro channel specimen-stuffing member may be integrally manufactured or may be manufactured by coupling glass substrates or plastic substrates. In case the electroporation apparatus is manufactured by coupling the plastic substrates, it is preferred that the electroporation apparatus should include an upper substrate (350a) and a lower substrate (350b), wherein the upper plate is formed with holes forming the wells, and the upper or the lower plate is formed with depressed channels.

Preferably, the electroporation apparatus according to the present invention is manufactured with a specimen-stuffing member whose length is 1 mm~10 cm. More preferably, the length of the specimen-stuffing member is 1 cm~5 cm. Preferably, the height of a channel, if the specimen-stuffing member has a channel structure, is 2 μm~2 mm, and the width thereof is 10 μm~10 mm. More preferably, the height of the channel is 20 μm~200 μm, and the width is 100 μm~5 mm. The electroporation apparatus having a channel structure according to the present invention can be manufactured by MEMS technique.

Figure 16:
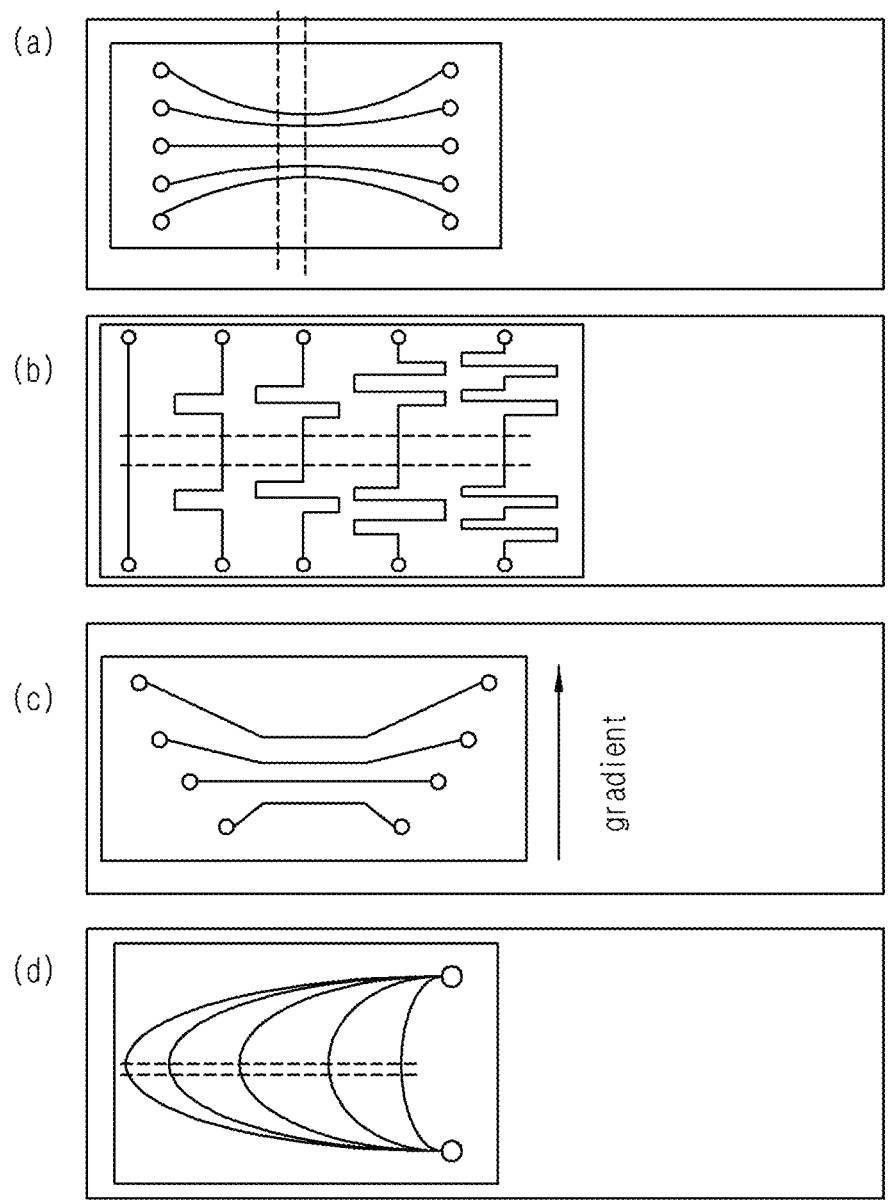
FIGS. 16, 17 and 18 illustrate an embodiment of an electroporation apparatus according to the present invention.

FIGS. 16 (a), (b), (c) and (d) illustrate various structures of an electroporation apparatus according to the present invention. FIGS. 16(a) to (c) illustrate structures wherein several pairs of wells for inserting electrodes of the pulse generator are formed at both sides, and each channel forming a space for connecting the plural pairs of wells and filling the specimen is formed for each pair of wells. Particularly, the electroporation apparatus illustrated in FIG. 16(c) is arranged with wells in such a manner that the distance of each pair of wells is different.

The electroporation apparatus illustrated in FIG. 16(d) is formed at both sides thereof with a pair of wells for inserting the electrodes of the pulse generator, and is also formed with a plurality of channels for connecting the pair of wells and filling the specimens.

Figure 17:
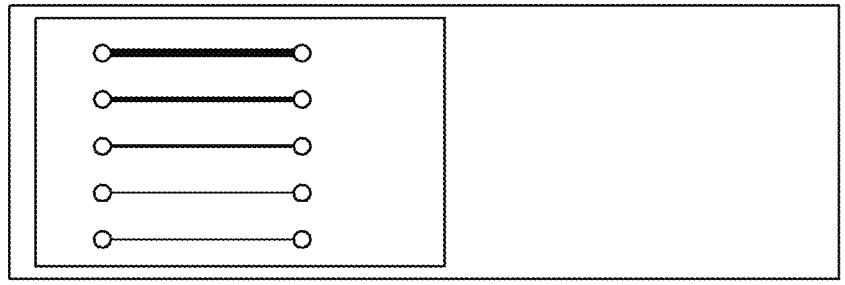

An electroporation apparatus illustrated in FIG. 17 is formed at both sides thereof with a pair of wells for inserting the electrodes of the pulse generator, and each pair of wells is formed with a channel, wherein each channel width is different from each other. If the channel length of each channel of the specimen-stuffing member is different, each channel can be applied with different electric field.

Figure 18:
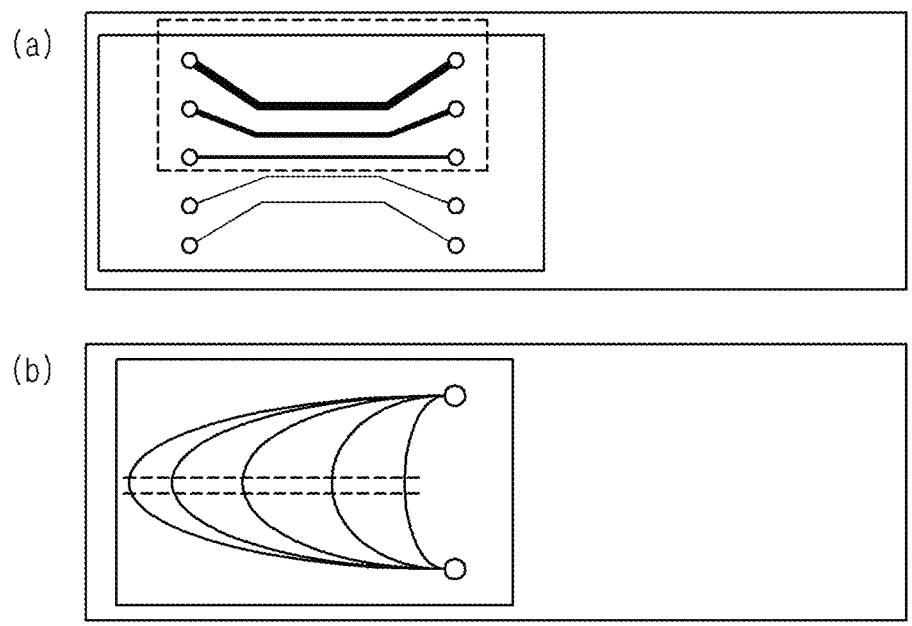

An electroporation apparatus illustrated in FIGS. 18(a) and (b) is such that each channel length and channel width connecting the corresponding wells are all different. The electroporation apparatus according to the present invention is such that a far less amount of current flows in the same electric field, compared with the conventional electroporation apparatus because the current flows only through the hollow specimen-stuffing member. As a result, power consumption can be minimized and if necessary, it can be manufactured for portable purpose using battery as a power source.

Hereinafter, an electroporation experiments and biological results using the electroporation apparatus and electroporation system according to the present invention will be described.

MODE FOR INVENTION

Preferred Embodiment

Preferred Embodiment 1

Electroporating Experiment of HEK-293 Cell Line Using Pipette Type Electroporation Apparatus 1-1. Preparation of Cells HEK-293 cell line (ATCC, CRL-1573) was stored in a medium supplemented with 10% FBS in a 25 cm² culturing flask, cultured in $CO_2$ incubator, and cultured up to 70% confluency. Next, the medium was removed, and the cell was washed using PBS buffer solution, and treated with trypsin. It was added by medium supplemented with FBS and centrifuged. Next, the cell was washed by PBS buffer solution, and suspended again in medium supplimented with 10% FBS to prepare a cell specimen.

1-2. Electroporation

Approximately 100 µl of HEK-293 cell specimen thus prepared at 1-1 was introduced into a reservoir at room temperature. The specimen of 100 µl was inserted with 5 µg of plasmid DNA pEGFP (obtained from: GenBank Accession: U55762; CLONTECH Lab.) as transfection material and mixed. A distal end of the specimen-stuffing member of the electroporation apparatus (see FIG. 8) according to the present invention was inserted into the mixed solution in the reservoir. A pipette-type pressure maintaining means was used to fill an interior of the specimen-stuffing member with specimens while the distal end of the specimen-stuffing member was so connected as to fluidly communicate with the mixed solution stored in the reservoir. The reservoir was replaced by a reservoir containing only the electrolytic solution and the distal end of the specimen-stuffing member was made to dip in the reservoir containing the electrolytic solution for fluid communication. In addition, electric field applying conditions such as pulse voltage, pulse duration and pulse repetition frequency and the like were set up. In the present experiment, it was so set up that an electric field of 0.57 kV/cm was once applied for a pulse duration of 30 ms. Next, an electric pulse was applied to the electrodes inserted into a connector out of the electroporation apparatus and the reservoir containing only the electrolytic solution under the electric condition.

1-3. Retrieve of Electroporated Cells

The specimen in the specimen-stuffing member was moved to a culture plate using a pipette and applied with medium. Cells were cultured in $CO_2$ incubator for 24-48 hours. The cells were counted and transfection rate thereof was measured.

1-4. Results

Figure 1:
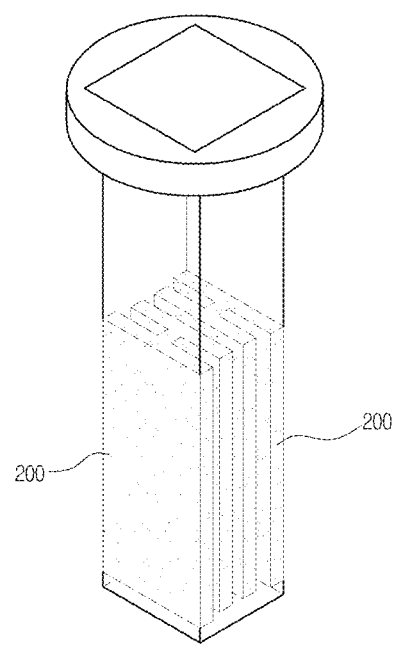
FIG. 1 is a representation of a cuvette equipped with parallel plate aluminum electrodes according to a conventional electroporation apparatus.
Figure 19:
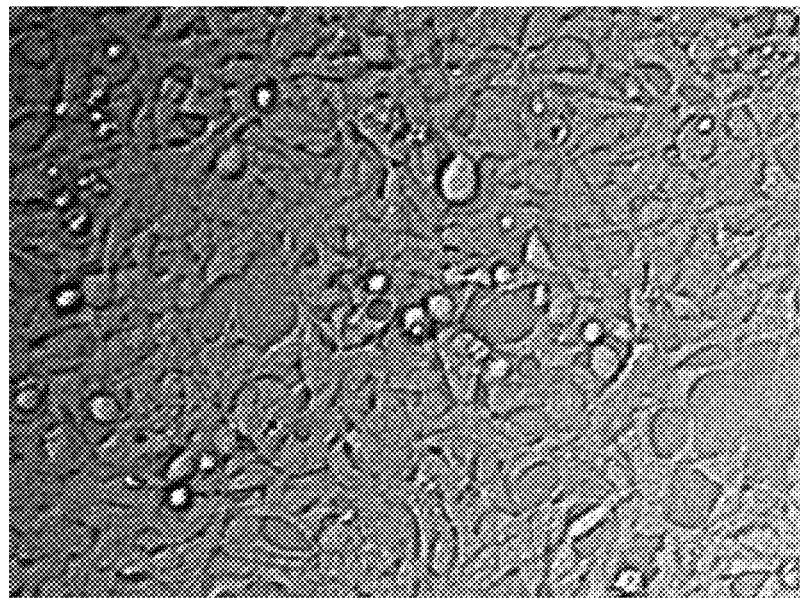
FIG. 19 is a microscopic photograph of cells electroporated by an electroporation apparatus according to the present invention, wherein the cells were observed via a bright field.
Figure 20:
FIG. 20 is a photograph observed in fluorescence relative to cells of the same region as those of the FIG. 19.
Figure 21:
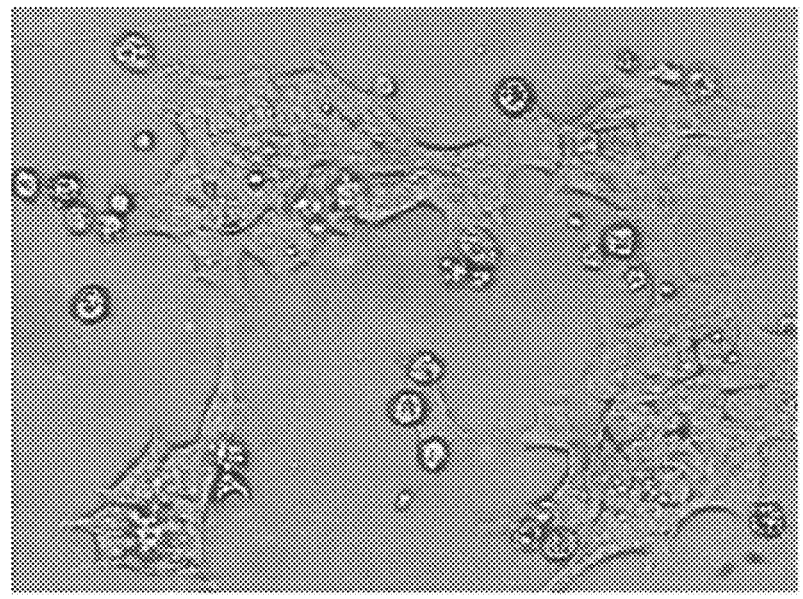
FIG. 21 is a microscopic photograph of cells electroporated by an electroporation apparatus according to the prior art, wherein the cells were observed via a bright field.
Figure 22:
FIG. 22 is a photograph in fluorescence of cells of the same region as those of the FIG. 21.

FIGS. 19 and 20 are microscopic photographs of HEK-293 cells into which plasmid DNA pEGFP was inserted by the electroporation apparatus according to the present invention. FIG. 19 is a photograph via bright field and FIG. 20 is a photograph observed in fluorescence. As a result of the experiment, the transfection rate (number of fluorescently expressed cells/number of surviving cells) was in the range of 90 to 95%, as shown in the photographs, and the survival rate of the cells was over 90%. FIGS. 21 and 22 are microscopic photographs of experimental results under the same condition as was done by using the conventional electroporation apparatus illustrated in FIG. 1 in which HEK-293 cells were transfected by plasmid DNA pEGFP. FIG. 21 is a photograph via bright field and FIG. 22 is a photograph observed in fluorescence. As a result of the experiment, the transfection rate was approximately 50% and the cell survival rate was observed to be less than that of the present invention. It could be noticed that dead or less-grown cells frequently observed in the prior arts (round-shape cells in FIG. 21) were drastically reduced in the result of the present invention (FIGS. 19 and 20). Therefore, it can be noted that the transfection rate and survival rate were much improved when an electroporation apparatus according to the present invention was employed. Furthermore, if the electroporation apparatus according to the present invention was used, it is easy to retrieve cells introduced with particular materials.

1-5. Effect Analysis Based on Geometrical Structure Changes of Specimen-Stuffing member HEK-293 cell specimen of approximately 100 µl prepared in 1-1 was infused into a reservoir at room temperature. Plasmid DNA pEGFP of 5 µg is added to the specimen of 100 µl as transfection material and mixed, and an experiment was conducted using the electroporation apparatus of FIG. 8. The specimen was picked up by a pipette-type pressure maintaining means, and reservoir was replaced by a reservoir containing only the electrolytic solution. A distal end of the specimen-stuffing member is dipped into the reservoir containing the electrolytic solution for fluid communication. The electric condition was set up in such a manner that an electric field of 425 V/cm was applied three times for a pulse duration of 10 ms. The electroporation was implemented in such a manner that the specimen-stuffing member of a capillary is fixed with a cross-sectional diameter of 0.135 cm while the lengths between the distal ends change from 0.4 cm to 4 cm. Table 1 shows the geometric conditions and experimental conditions.

TABLE 1

| L (cm) | D (cm) | A (cm²) | R (cm⁻¹) | voltage | cell counting | Transfection rate |
|---|---|---|---|---|---|---|
| 4 | 0.135 | 0.014307 | 279.6 | 2500 | 160/163 | 98.0 |
| 3.6 | 0.135 | 0.014307 | 251.6 | 2250 | 138/142 | 97.0 |
| 3.2 | 0.135 | 0.014307 | 223.7 | 2000 | 122/127 | 96.0 |
| 2.8 | 0.135 | 0.014307 | 195.7 | 1750 | 158/165 | 96.0 |
| 2.4 | 0.135 | 0.014307 | 167.8 | 1500 | 117/124 | 94.0 |
| 2 | 0.135 | 0.014307 | 139.8 | 1250 | 107/117 | 91.0 |
| 1.6 | 0.135 | 0.014307 | 111.8 | 1000 | 104/117 | 89.0 |
| 1.2 | 0.135 | 0.014307 | 83.9 | 750 | 46/63 | 73.0 |
| 0.8 | 0.135 | 0.014307 | 55.9 | 500 | 43/62 | 69.0 |
| 0.4 | 0.135 | 0.014307 | 28.0 | 250 | 18/68 | 26.0 |

In the above table, L denotes a longitudinal length (cm) of the specimen-stuffing member, D denotes a diameter (cm) of cross-section, A denotes an area (cm²) of the cross-section, and R $(cm^{-1})$=L/A.

Following the electroporation under the condition thus described, the specimens in the specimen-stuffing member were moved to a culturing plate and cultured for 24 hours. The cells were counted and the transfection rate was measured. FIG. 22 shows a result thereof.

Figure 23:
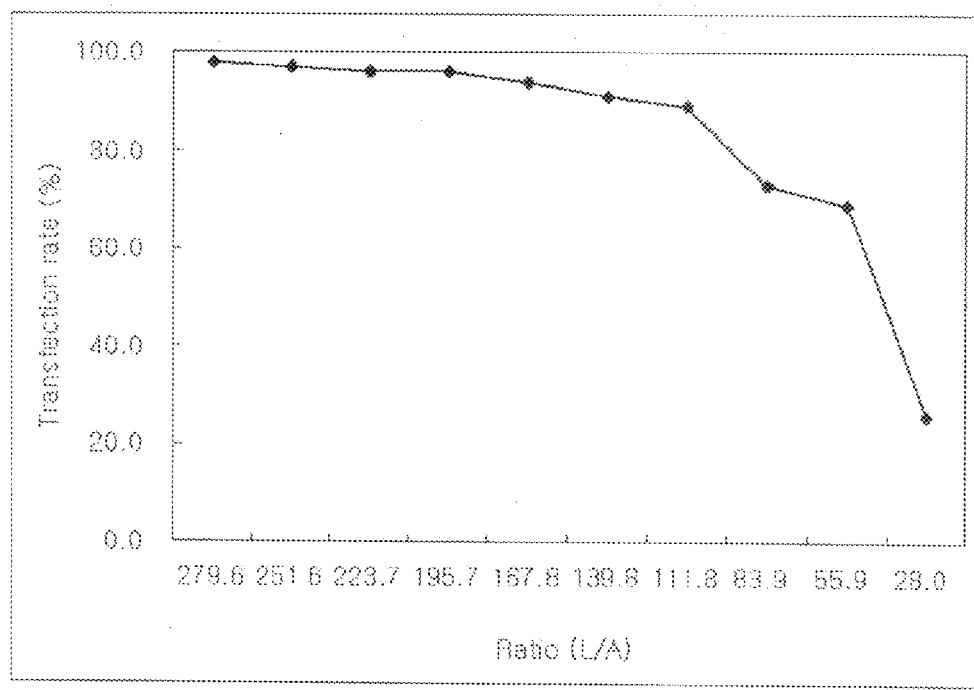
FIG. 23 illustrates a graph which shows a relation between geometric shape of a specimen-stuffing member and electroporation efficiency in an electroporation using an electroporation apparatus according to the present invention.
Figure 24:
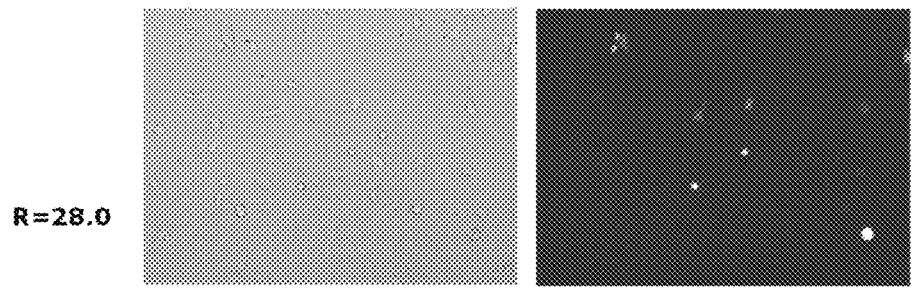
FIGS. 24 to 33 are microscopic photographs suggesting a relation between geometric shape of a specimen-stuffing member and an electroporation efficiency in an electroporation using an electroporation apparatus according to the present invention.
Figure 25:
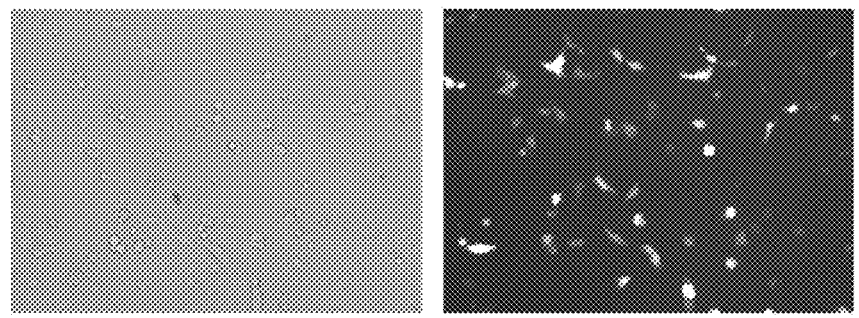
Figure 26:
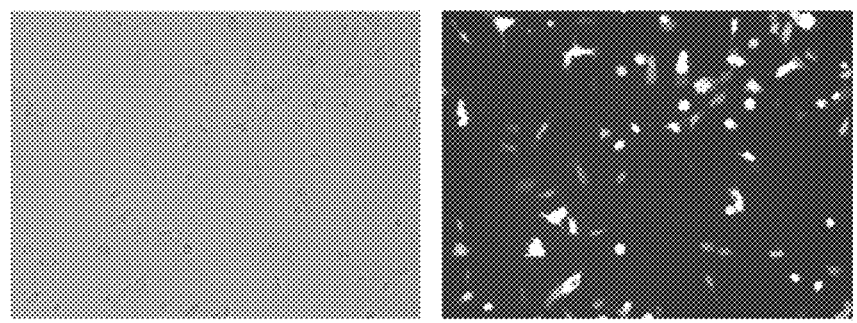
Figure 27:
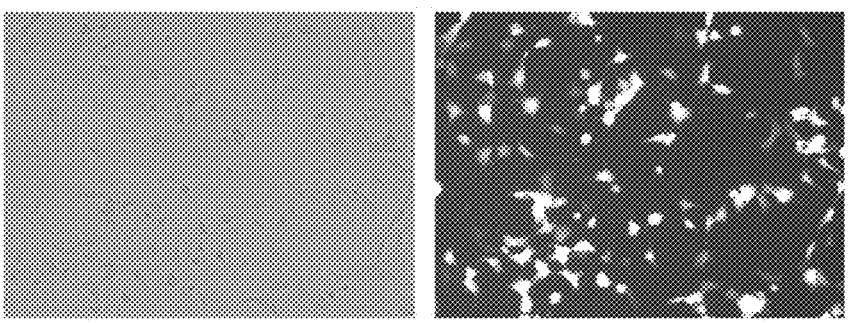
Figure 28:
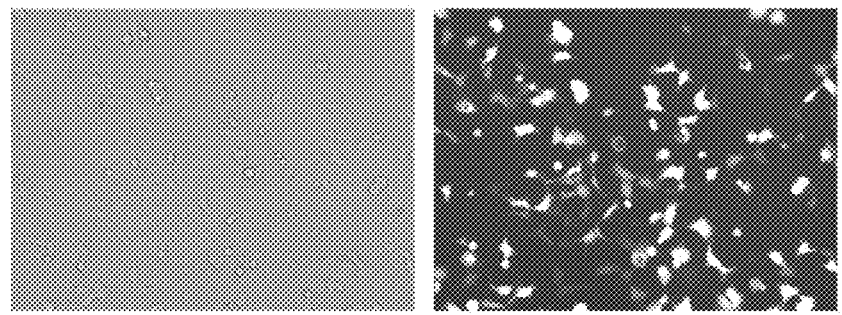
Figure 29:
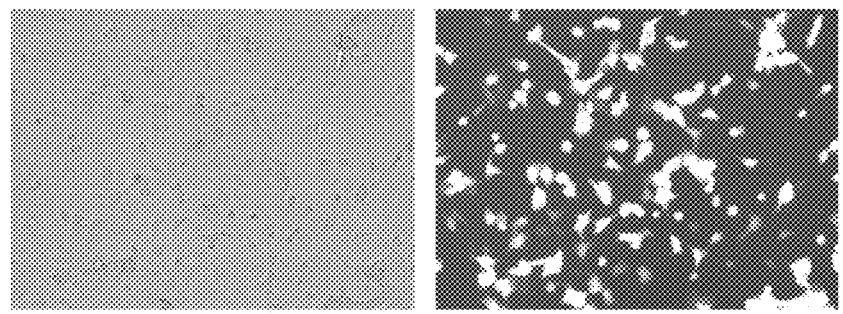
Figure 30:
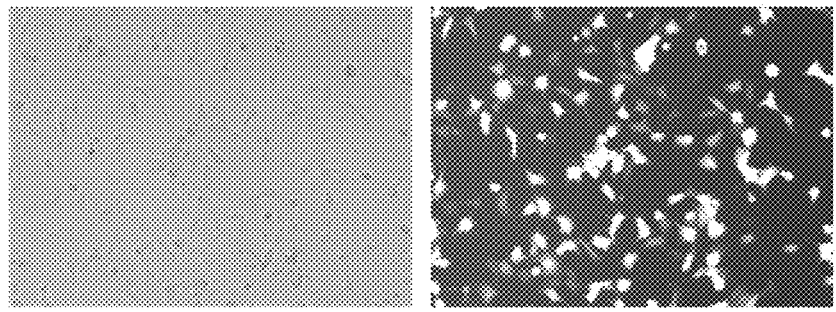
Figure 31:
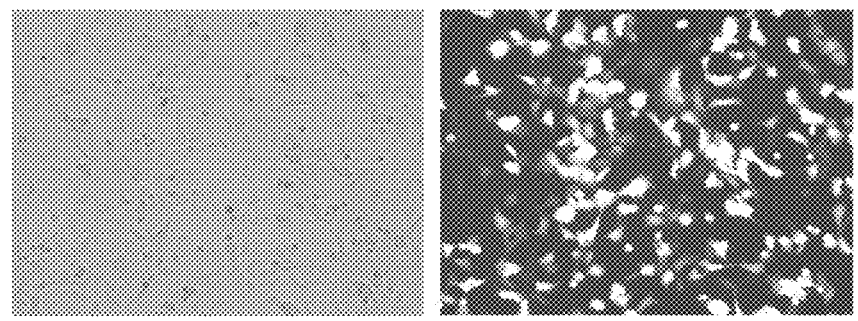
Figure 32:
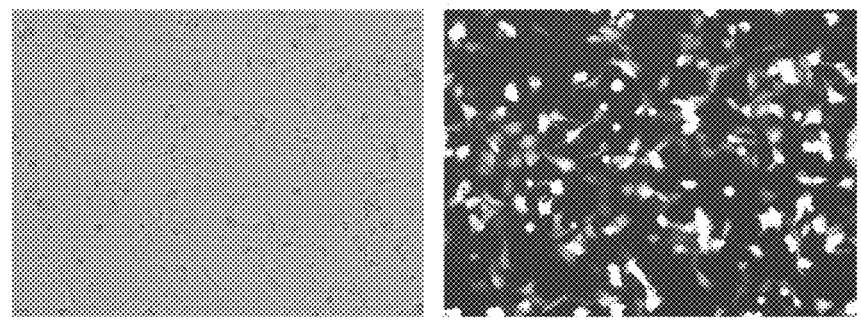
Figure 33:
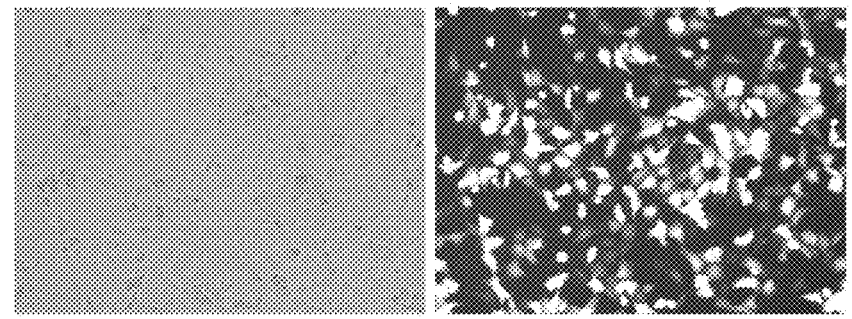

FIG. 23 illustrates a graph in which transfection rate was greatly reduced when R is below 50. FIGS. 24 to 33 are microscopic photographs of HEK-293 cells into which plasmid DNA pEGFP was inserted by the electroporation apparatus according to the present invention. Left side of each figure is a photograph observed via bright field, and right side is a photograph observed in fluorescence.

1-6. Electroporation Experiments Using Various Cell Lines

Figure 34:
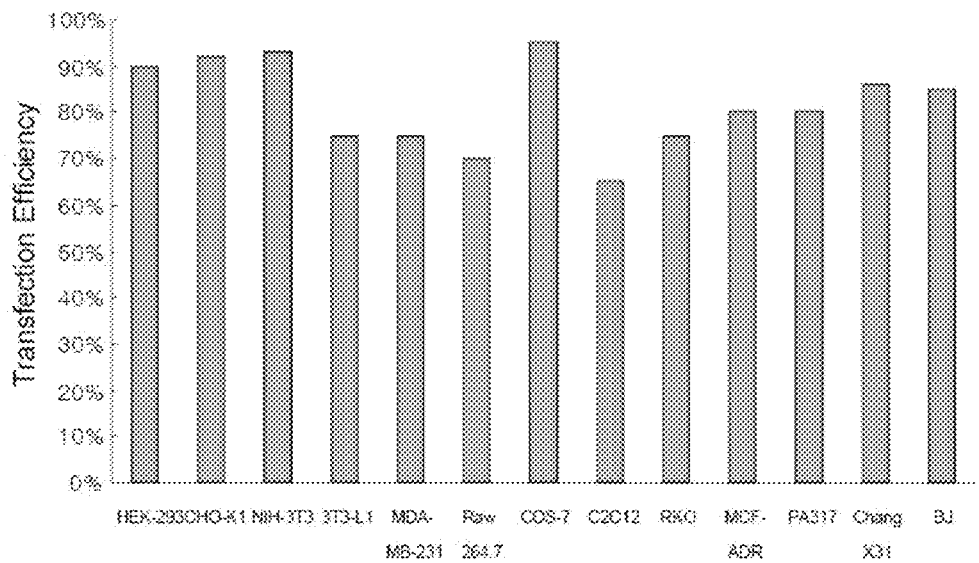
FIG. 34 illustrates a graph wherein an electroporation is conducted relative to various cells according to the present invention and transfection rate (number of fluorescently expressed cells/number of surviving cells) by GFP expression is obtained.
Figure 35:
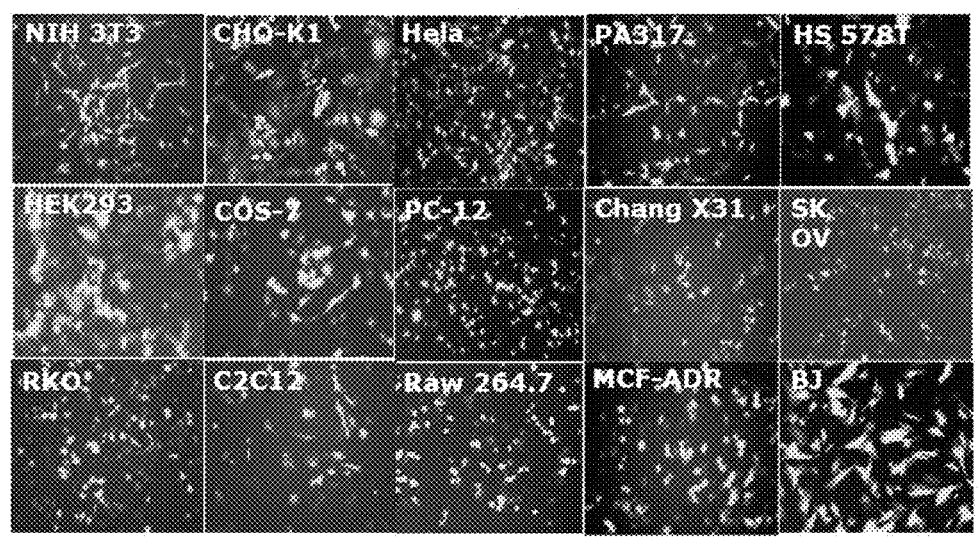
FIG. 35 is a microscopic photograph for illustrating a result of FIG. 34.

The electroporations were conducted in the same conditions with various cell lines. The experimental results, as shown in FIG. 34, are such that all the cells described in Table 2 showed an excellent transfection rate by the electroporation apparatus according to the present invention. FIG. 34 shows a transfection rate given in a graph, and FIG. 35 illustrates a microscopic photographic result relative to GFP expression.

TABLE 2

|  | ACC. No. | origin | Tissue |
|---|---|---|---|
| HEK293 | ATCC: CRL-1573 | Human | Embryonic kidney |
| CHO-K1 | ATCC: CRL-9618 | Hamster | Ovarian |
| NIH3T3 | ATCC: CRL-1658 | Mouse | Fibroblast |
| 3T3-L1 | ATCC: CL-173 ™ | Mouse | Pre-adipocyte |
| MDA-MB-231 | ATCC: HTB-26 | Human | Breast |
| Raw264.7 | ATCC: TIB-71 | Mouse | Macrophage |
| Cos07 | ATCC: CRL-1651 | Monkey | Kidney |
| C2C12 | ATCC: CRL-1772 | Mouse | Myoblast |
| RKO | ATCC: CRL-2577 | Human | Colon |
| MCF-ADR | ATCC: HTB-22 | Human | Breast |
| PA317 | ATCC: CRL-9078 ™ | Human | Embryonic firoblast |
| ChangX31 | ATCC CCL-13 ™ | Human | Liver |
| BJ | ATCC: CRL-2522 | Human | Foreskin Primary culture |

1-7. Transfection of siRNA

Figure 36:
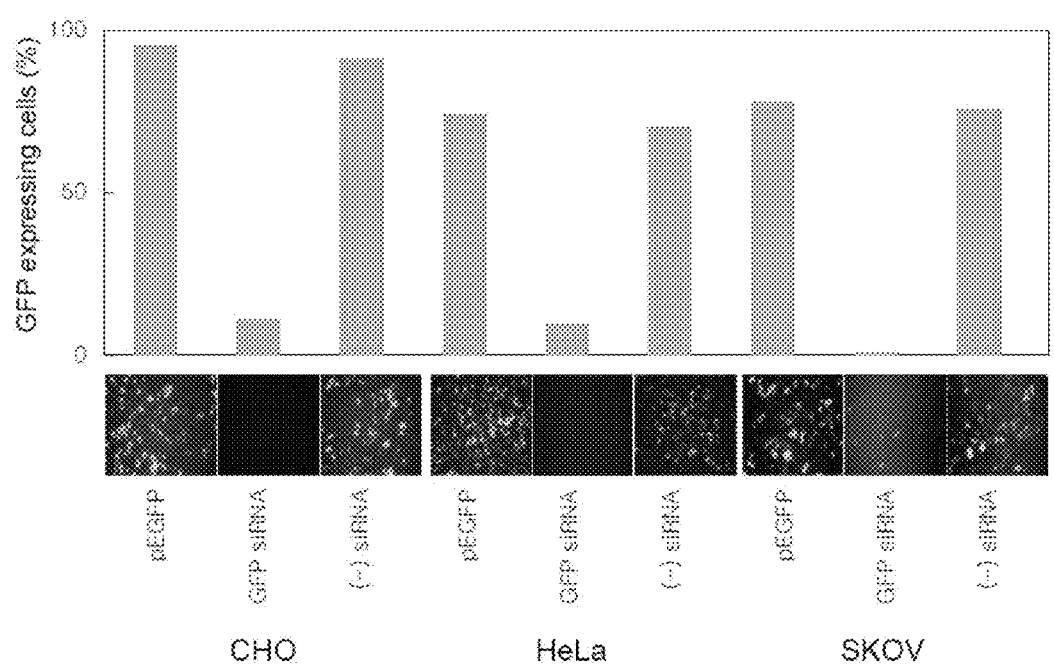
FIG. 36 illustrates a result wherein GFP siRNA and pEGFP are simultaneously transfected into cells by way of an electroporation according to the present invention and GFP expression thereof is measured by a microscope.

CHO cell line (ATCC:CRL-9618), HeLa cell line (ATCC, CCL-2) and SK-OV-3 cell line (ATCC, HTB-77) were employed for experiments. The electroporation was conducted in the same ways as in those of 1-1 to 1-4 to observe the GFP expression except that GFP siRNA (Ambion, NO. 4626, USA) of 0.25 nmol and pEGFP 5 of μg as transfection materials were mixed with a specimen of 100 μl. As illustrated in FIG. 36, GFP expression was barely observed when employed with a mixed solution of GFP siRNA and pEGFP as transfection materials, which suggests that pEGFP and siRNA were all effectively transmitted within the cells and thereby the GFP expression was inhibited by the siRNA in the cells.

Preferred Embodiment 2

Electroporating Experiment of SK-OV-3 Cell Using a Channel-Structured Electroporation Apparatus 2-1. Manufacturing of Micro Channel Structure In the preferred embodiment 2, a biological experiment was conducted employing an electroporation apparatus having a specimen-stuffing member of a micro channel structure. An electroporation apparatus disposed with wells for inserting electrodes and channels as hollow specimen-stuffing members for connecting the wells was manufactured by a method such as molding or the like. The channel structured specimen-stuffing members were variably manufactured with 20 μm in height, 2 cm in length and 100 to 500 μm in width of the channel. However, it should be apparent that the channel pattern was formed by photolithographic method using photomasks. For example, first of all, negative photoresist (SU-8, MicroChem, Massachusetts, USA) is spin-coated on a silicon wafer to form a mold master of 20 μm thickness. The soft baking is performed to make the mask pattern on the SU-8 coated silicon wafer by the mask aligner (MA-6, Karl Suss GmbH, Germany). SU-8 pattern is exposed to light, and post-exposure bake, development and hard baking process are performed. Then, mixture (Sylgard 184, DOW Corning Co., USA) of PDMS and cure agent is poured on the pattern. The curing condition is 90° C. for 30 minutes. The PDMS layer processed by 25 W oxygen plasma is coupled to a glass substrate to form a micro channel.

2-2. Cell Preparation and Culture

SK-OV-3 cell (ATCC, HTB-77) was cultured in an $CO_2$ incubator of 37° C., humidity 5% using DMEM (Dulbecco's modified Eagle's Medium) supplied with heat inactivated Fetal Bovine Serum(FBS, Sigma), penicillin (100 unit/ml), streptomycin (100 μg/ml) and L-glutamine (4 mM). Trypsin-EDTA was used to separate cells from 25 $cm^2$ tissue culturing flask. The final cell suspension concentration was adjusted to $1 \times 10^7$ cells/ml. The survival rate of cells following the application of pulse was used as a direct proof of viability. Before the electric pulse is applied, PI (propidium iodide) was added to cell medium. PI is a conventionally used fluorescent marker. The PI is an indicator of cell membrane introduction in a living cell and is inserted into nucleic acid. If the cell membrane is permeable, the PI enters the cell, and is combined with nucleic acid to emit a red fluorescence. As the intensity of the red fluorescence is determined by the amount of PI combined with the nucleic acid, it is possible to perform quantitative analysis. In the present experiment, PI 1.0 mg/ml was applied to cell medium in the ratio of 1:20 (v/v).

Because GFP (green fluorescent protein) extracted from *Aequorea victoria* has a higher visibility and emission of effective inner fluorophore, it is variably used in the fields of biochemistry and cell biology. The GFP is used as a gene expression marker of protein targeting in cells and organs. In the present experiment, plasmid isolation kit (Promega, USA) was used for extracting and refining pEGFP-N1 plasmid for transmitting GFP of colitis germs *E. coli*. The extracted plasmid DNA was checked on an agarose gel by way of electrophoresis. The concentration of the plasmid was determined by measuring the absorbance at 260 nm with a spectrophotometer. Before the pulse was applied, plasmid pEGFP-N1 was applied to a specimen in the concentration of 0.1 μg/μl. A reporter gene expression was used as evaluation of successful transfection. In order to inspect the expression, cells exposed to electric pulse were cultured. After the pulse was applied, the channel structured electroporation apparatus was dipped in the DMEM medium, and placed in an incubator for 24 hours before EGFP expression inspection. For cell culture, no prior process was conducted except for $O_2$ plasma to the micro channel device.

2-3. Electroporation

Figure 2:
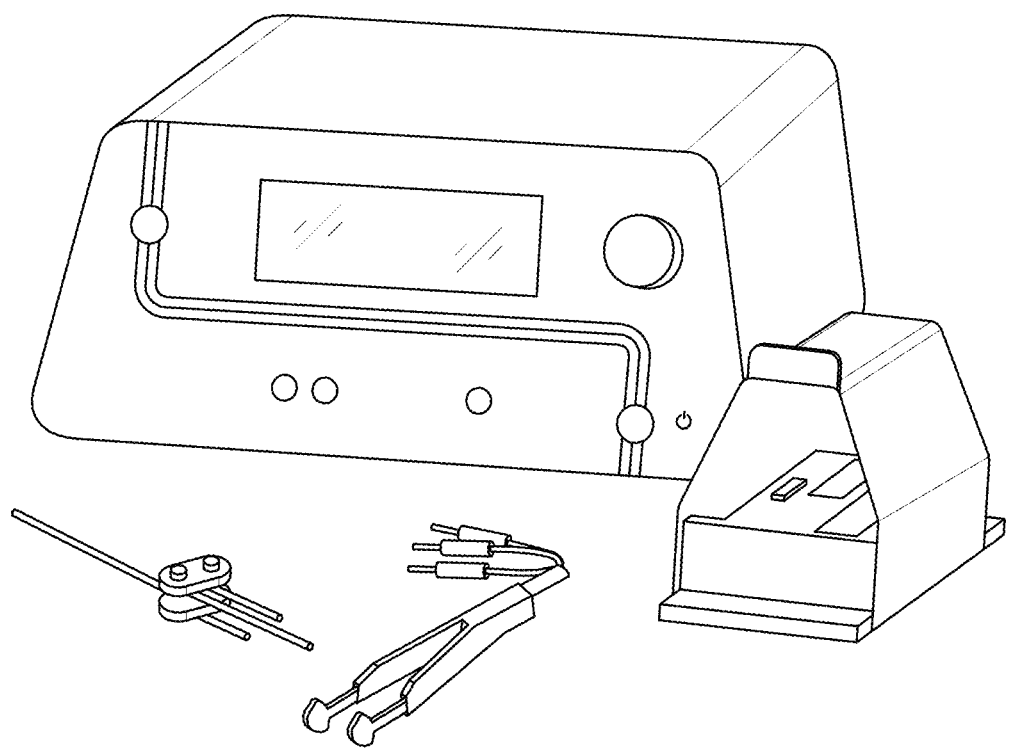
FIG. 2 is a photograph of a conventional electroporation apparatus which is a square wave electroporation apparatus (ECM 830, BTX, USA).

A system for electroporation comprises the aforementioned 2-1 electroporation apparatus having a channel structured specimen-stuffing member, home-made high voltage pulse generator, Pt electrodes and an electrode holder. The cell specimens prepared in the aforementioned 2-2 were introduced into one well to allow the channel type specimen-stuffing members to be filled with cell specimens or to allow an excess quantity of specimen to be filled in other wells by capillary or water head pressure action, or to allow the wells and specimen-stuffing members to be infused by pumping. By fixing the electrode holder on the microscope, the electro-permeating process could be observed under application of electric pulse. The high voltage pulse generator was connected to a computer via an analogue output board (COMI-CP301, Comizoa, Korea), and was controlled by LabVIEW ver 6.1 (National Instrument, USA) program. In order to verify the performance of the electroporation apparatus according to the present invention, our experimental results were compared with those of square wave electroporation apparatus (ECM 830, BTX, USA, see FIG. 2) and cuvette of 2 mm gap equipped with parallel aluminum electrodes (see FIG. 1). In order to analyze the performance of said two systems under the same electric field (1 kV/cm), the cuvette was applied with an voltage of 200 V, and the micro channel device according to the present invention was applied with an voltage of 2 kV. The channel width was changed as 100 μm, 200 μm, 300 μm, 400 μm, and 500 μm, and experiments were conducted using PI relative to the five cases. For GFP transfection and expression, experiments were carried out for 10 ms under various pulse conditions from 0.75 kV/cm to 0.25 kV/cm. In order to observe PI absorption, a reverse phase fluorescent microscope (LX790, Olympus, USA) equipped with 100 W mercury lamp and x20 object lens (0.4 NA) was used. The light was optically filtered by a 530±20 nm band pass filter, and the fluorescence induced from the electroporated cells was filtered by 590 nm long pass filter. Image of resolution 640×80 pixels were obtained with a rate of 15 frames/sec using 12-bit CCD camera (PCO, Kelheim, Germany). The exposed time of 10 ms was given for all the cases. In order to observe the fluorescence relative to cell viability and GFP transfection, the excited light was filtered by 475±5 nm band pass filter, and the induced fluorescence was filtered by 520 nm long pass filter. Images of resolution 640×80 pixel were obtained using a color 31T CCD camera (AW-E300, Panasonic, USA).

2-4. Results

Figure 37:
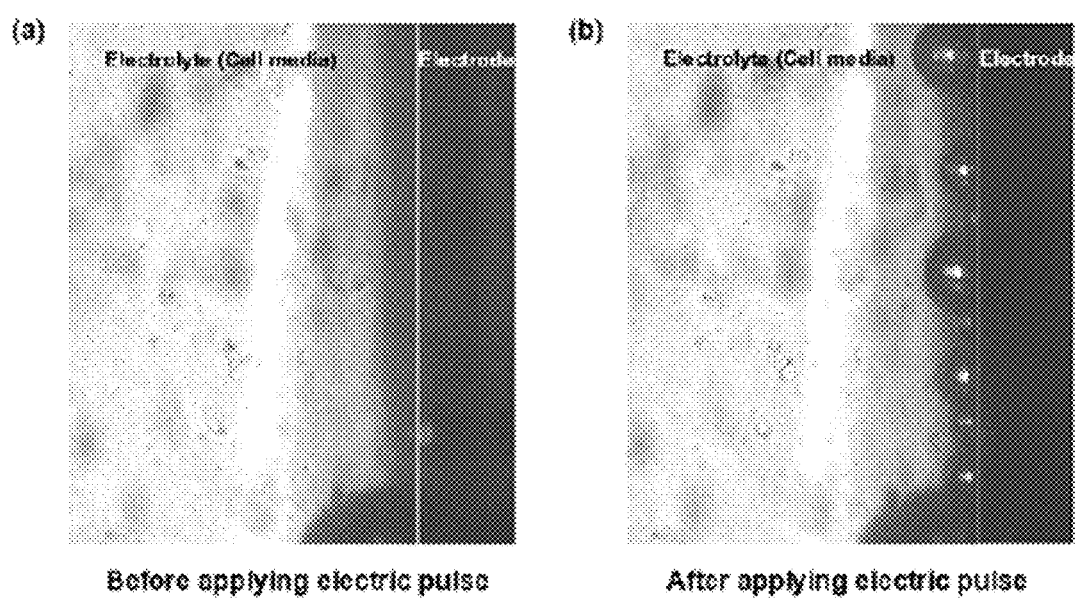
FIG. 37 illustrates an Al electrode surface before (a) and after (b) the application of electric pulse when a cuvette equipped with a conventional Al electrode is used to perform an electroporation.

When an electric pulse was applied in the cuvette using Al electrodes (see FIG. 1), air bubbles were electrochemically generated on the surfaces of the electrodes to form two layers of liquid and gas phases. FIG. 37 illustrates an Al electrode surface before (a) and after (b) the application of electric pulse when a cuvette equipped with a conventional Al electrode is used to perform an electroporation. FIG. 37(b) shows air bubbles formed on the electrode surface. The air bubbles are created very fast and generate a complicated liquid movement. The said air bubble movement, in cooperation with the electrophoresis during pulse application, results in an uneven state of bulk media and cells. Furthermore, aluminum is a material easily formed with an oxide layer ($Al_2O_3$), which acts as a high resistance layer. In the electroporation apparatus according to the present invention, the air bubble formation or the complicated medium movement was not found, which explains that the electrodes positioned only on both the distal ends and the chemical stability of the electrode material (Pt) used in the present invention prevent the air bubble formation from directly influencing on the specimens. As a result, although the bulk medium movement in the cuvette wherein the air bubbles are created is strong, the medium in the electroporation apparatus having a channel structure according to the present invention can maintain a stable condition because of less air bubble influence. The micro channel structure according to the present invention is excellent in visualization and is not visually affected by electrodes, such that mechanism of the electroporation can be visually studied using microscopes and the like.

2-5. Intercalation Rate and Electro-Permeability Process Inspection

Figure 38:
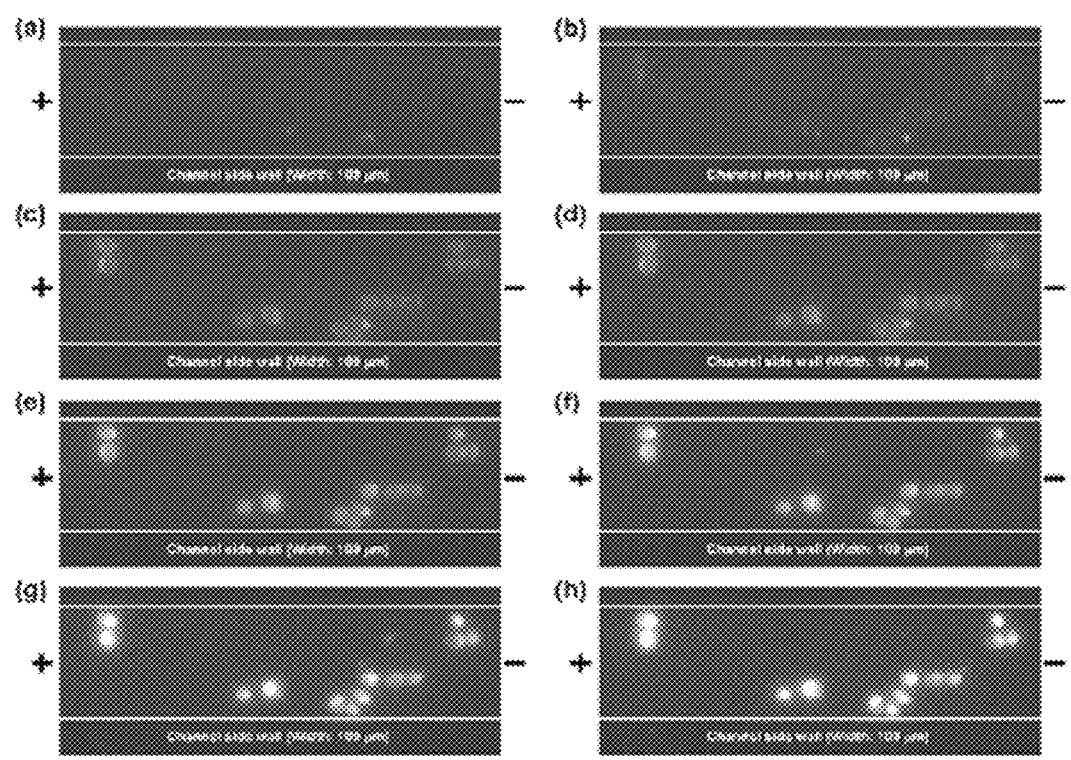
FIG. 38 illustrates an infusion process of PI (propidium iodide) in a 100 μm to width micro channel.

A local introduction of PI during the milli-sec (ms) unit in the channel was observed after a pulse was applied to the electroporation apparatus having a micro channel specimen-stuffing member according to the present invention. If the same scope of electric field is applied in the conventional system, the PI permeability process was detected from almost all the cells within the micro channel. FIG. 38 illustrates an infusion process of PI in a 100 on width micro channel. Right after the application of pulse, PI was infused only from an anode direction. As time goes by, the fluorescence was dissipated all over the interiors of the cells (c to d), and after 10 seconds, the nucleic acid started to radiate fluorescence (e to h). Observation directly reflects the PI characteristics coupling to the nucleic acid. The function of observing in real time in a single living cell is very advantageous because it can provide an important information about the basic cell process. For example, by way of detecting FRET (fluorescence resonance energy transfer), the oligo DNA pair in the cytoplasm can be observed in being combined with c-fos mRNA. Because it can be directly observed in real time, the micro channel device according to the present invention is very useful.

Figure 39:
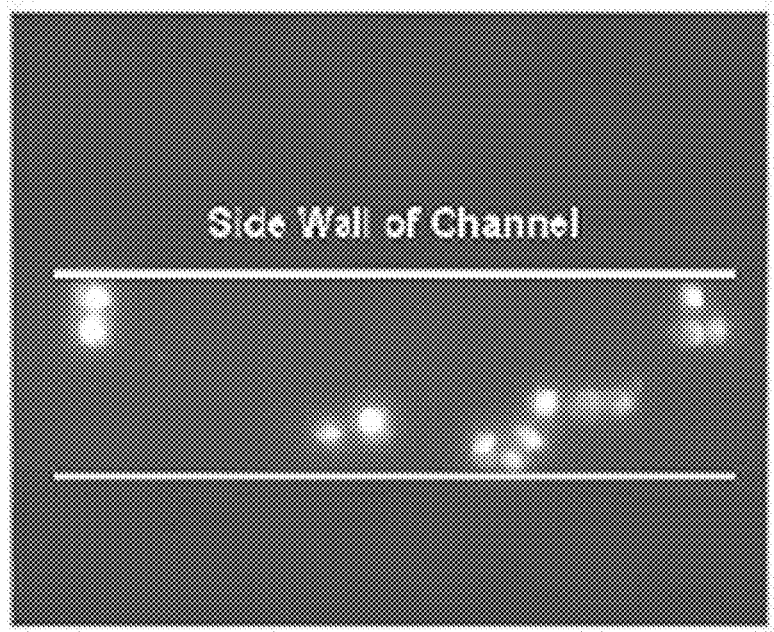
FIG. 39 is a microscopic photograph of cells infused by PI via an electroporation in two micro channels each having a different channel width of 100 μm(a) and 500 μm(b), respectively.
Figure 39:
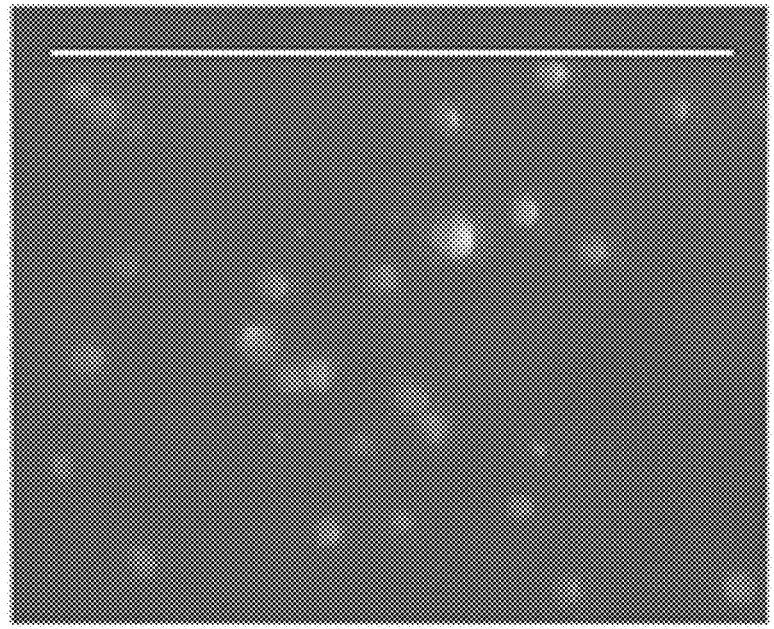
Figure 40:
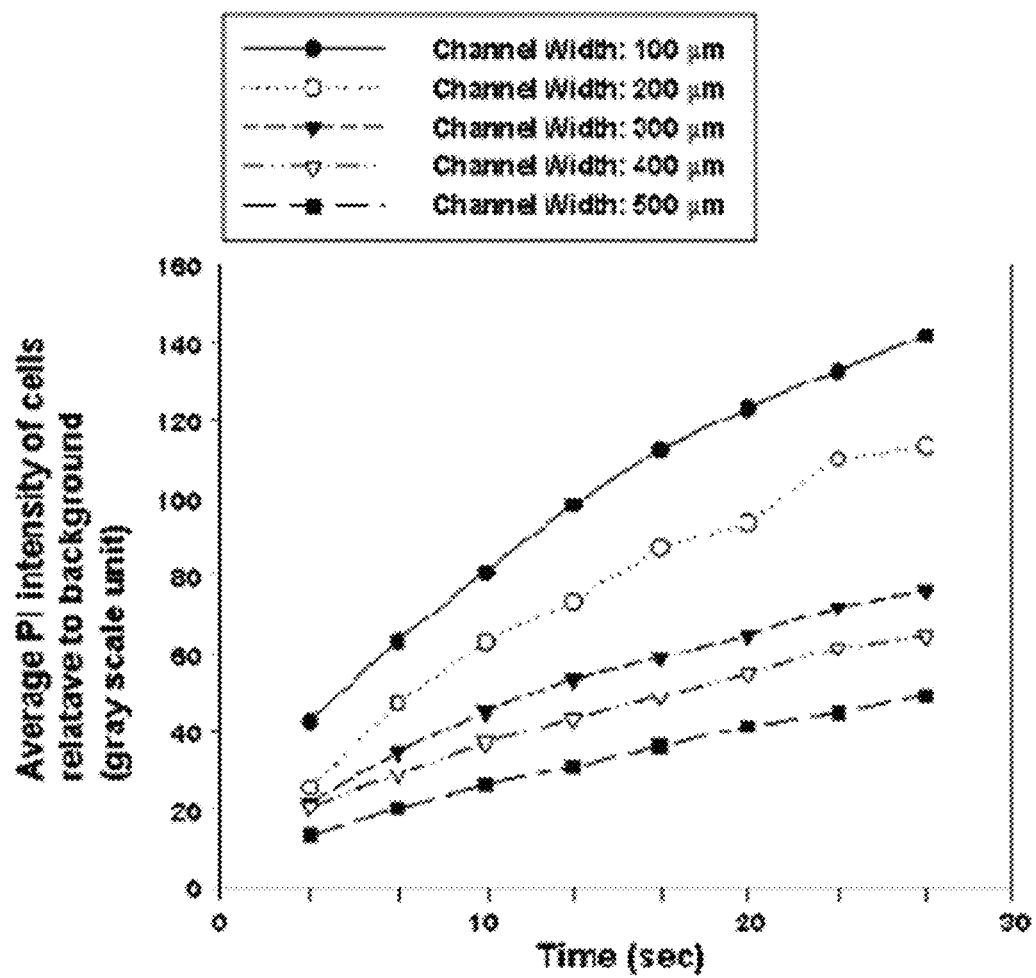
FIG. 40 is a graph comparing an light emitting intensity of PI according to the channel width.
Figure 41:
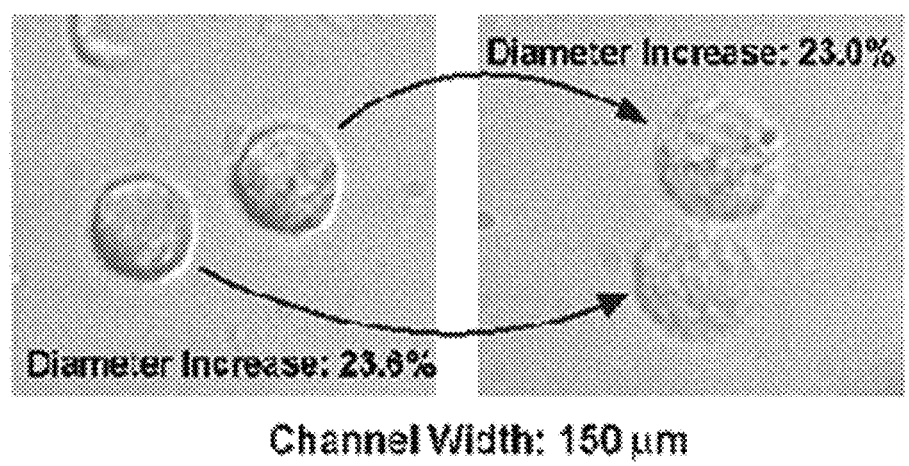
FIG. 41 illustrates cells size change before and after an electroporation in two micro channels, each having a different channel width of 150 μm(a) and 500 μm(b) respectively.
Figure 41:
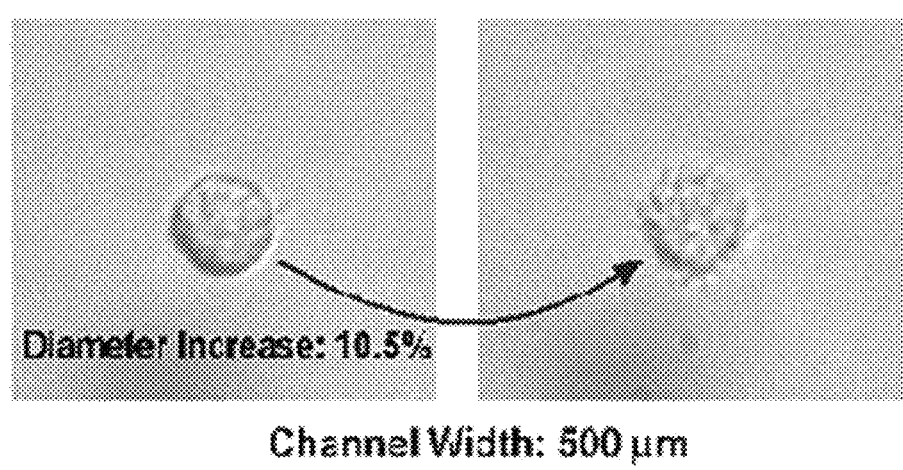

2-6. Electroporation Effect Based on Channel Width Changes in Electroporation Apparatus Having a Micro Channel Specimen-Stuffing Member In the electroporation apparatus, the intensity of fluorescence relative to dye absorption is differently observed according to the channel width. If the same electric pulse is applied, the intensity of grey scale unit relative to the cell region decreased as the channel width increased. FIG. 39 is a microscopic photograph of cells infused by PI via electroporation in two micro channels each having a different channel width of 100 μm(a) and 500 μm(b) respectively after 30 seconds of pulse application, wherein the electric field was 1 kV/cm, and pulse duration was 10 ms. It was confirmed that PI absorption of cells in a micro channel having a narrow channel width (100 μm) is much greater than that of cells in a micro channel having a broader channel width (500 μm). In order to compare the PI absorption relative to five micro channels each having a different channel width, images were photographed at 15 frames/sec during the experiments. Image process was conducted at every 50 frame. By using graphic software (Paint Shop Pro 7.0, Jaw Software, USA) and MATLAB program (MathWorks, Inc., USA), an average intensity of the grey scale unit for the background was subtracted from the grey scale unit for the cell region. A comparative data relative to the PI intensity is illustrated in FIG. 40. It can be noticed that the channel width affects the PI absorption. Because the geometric parameters except the electrode gap in the cuvette based system were not seriously considered, the said phenomenon in the micro channel specimen-stuffing members should be given a special attention. The effect of the electric pulse to the cells was analyzed in bright field. The bright field analysis method was conducted under two conditions of 150 ani and 500 on widths. The pulse conditions are the same as those of other experiments (10 ms in 1 kV/cm electric field). Images following the exposure to the electric pulse were obtained 25 seconds after the pulse application. Exposed to the electric pulse, the cells were immediately swelled. FIG. 41 illustrates a cell size change before and after an electroporation in two micro channels, each having a different channel width of 150 μm(a) and 500 μm(b), respectively. By using AutoCAD 2002 (Autodesk, Inc., USA), the cell diameter increase was measured and increased rate relative to diameter before the pulse application was calculated. Although the cell diameter at 150 μm channel width increased approximately by 23%, the cell diameter at 500 μm channel width increased approximately by 10%. The said difference relative to the channel width seems to be resulted from the different degrees in electroporation. From these results, it was confirmed that geometrical shapes of channel cross-sections such as channel widths or heights during the electroporation of micro channel specimen-stuffing members should be considered.

2-7. Cell Culture in PDMS Channel Specimen-Stuffing Member

Figure 42:
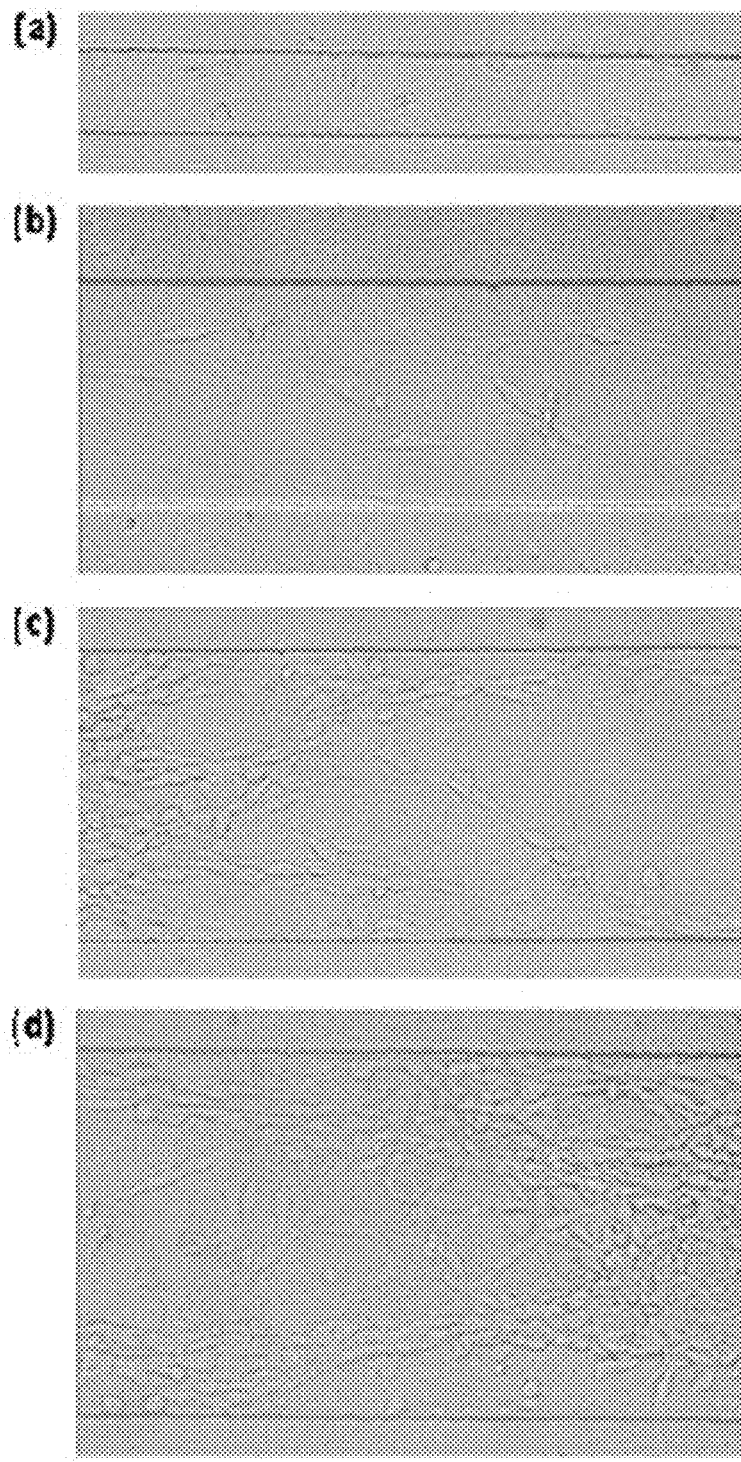
FIG. 42 illustrates a result wherein cells were cultured for seven days in micro channels each having a different channel width of 50 μm(a), 150 μm(b), 200 μm(c) and 250 μm(d), respectively.

PDMS is a material appropriate for the cell culture system of channel device due to its biological suitability and permeability. Because it usually takes 24 hours to express in cells following the electroporation in EGFP transfection experiment, it is necessary to have a cell culture function in the EGFP transfection experiment in the channel specimen-stuffing member according to the present invention. Inspection was made as to whether the channel specimen-stuffing member could be used as a reservoir for cell culture. Cells were infused into the channel and the entire PDMS channel device was dipped into the cell medium (DMEM), and stored in an incubator for 7 days. FIG. 42 illustrates a culture result thereof. Only the $O_2$ plasma process for coupling PDMS to the glass was conducted in the PDMS channel device. Following 7 days, as a result of observation on the wells and cells at the distal ends of the channel, it could be noticed that the cells were well dispersed on the floor surface and maintained an excellent condition. The cells in the central channel of 50 μm channel width still survived, but conditions thereof were not good (see FIG. 42(a)). It seems that the cell culture was ill affected by lack of fresh culture media and $CO_2$, and cramped physical space caused by narrow channel width relative to the channel length. FIGS. 42 (b), (c) and (d) also illustrate a result wherein cells are cultured for seven days in a micro channels each having a different channel width of 150 μm, 200 μm and 250 μm respectively. It could be noted that the cells were attached, dissipated and successfully moved in a broader micro channel. As a result of the aforementioned experiment, it was confirmed that the cell culture was possible in the electroporation apparatus according to the present invention. This shows that many advantages could be provided along with the real time visualization function in the study of various cells for a long time. Furthermore, the electroporation apparatus according to the present invention could be expectedly used in simultaneously tracing the routes of multiple proteins within a living cell for a long time by using nano-sized quantum dot semiconductor.

2-8. EGFP Expression in SK-OV-3 Cell

Figure 43:
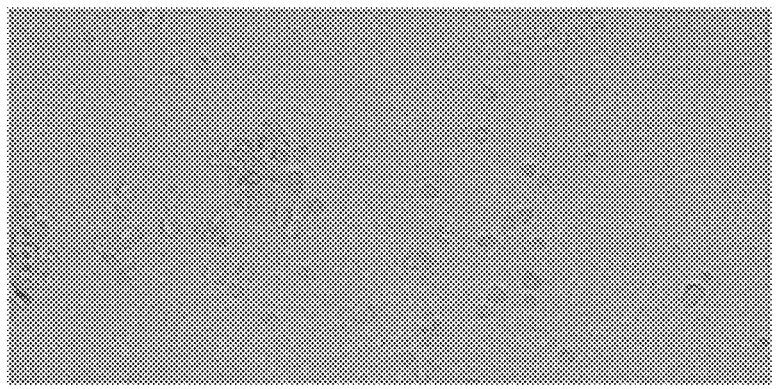
FIG. 43(a) is a photograph observed via a bright field of cells through which a 0.75 kV/cm of electric field was applied for 10 ms and 24 hours elapsed.
FIG. 43(b) is a photograph observed via an overlap of bright field and fluorescence of cells through a 0.4 kV/cm of electric field which was applied for 10 ms and 24 hours elapsed.
FIG. 43(c) is a photograph of cells of FIG. 43 (b) observed in fluorescence.
Figure 43:
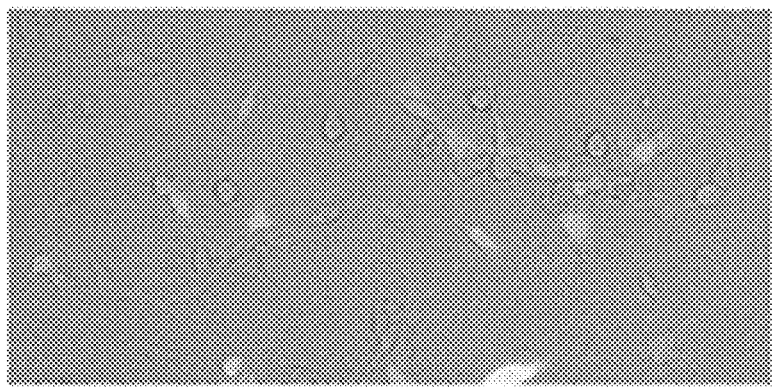
Figure 43:
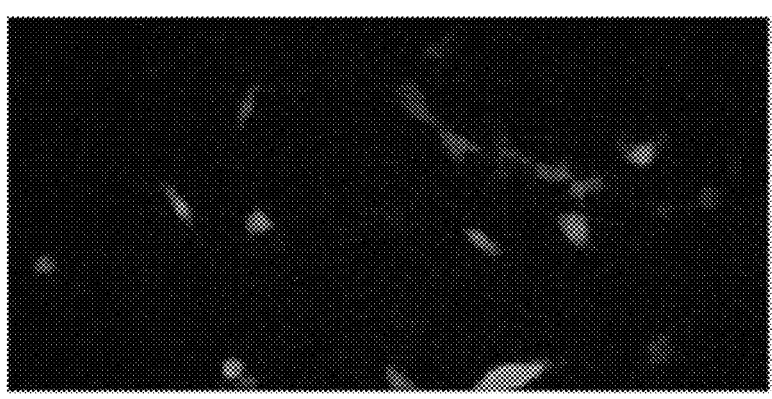

A biological experiment was carried out by EGFP which is widely used as gene expression marker. First of all, an electric pulse of 1.5 kV was applied to induce an electric field of 0.75 kV/cm for 10 ms. This is an adequate condition for infecting SK-OV-3 cells using currently marketed BTX electroporation apparatus. The said electric field condition was too harsh for cells in the channel structured specimen-stuffing members. The cells were inspected after 24 hours and a result thereof is illustrated in FIG. 43 (a). It could be noticed that the cells are not under an excellent state to be dissipated on the floor surface. The fluorescence was not detected. The electric field adequate for the currently marketed electroporation apparatus is too strong to be adopted for the channel structured electroporation apparatus according to the present invention, so the electric field was changed in the range of 0.25 kV/cm to 0.75 kV/cm in the present experiment. As a result thereof, the cells were successfully infected in the range of 0.4 kV/cm to 0.5 kV/cm, and it was confirmed that green fluorescence was expressed. The most preferable condition was 0.4 kV/cm. FIGS. 43 (b) and (c) show the result thereof. From this result, it was verified that the energy efficiency for electroporation in the electroporation apparatus according to the present invention is far more excellent than that of using the cuvette-type electroporation apparatus.

As mentioned earlier, the infusing process can be visualized in real time using the same electroporation apparatus according to the present invention. In the electroporation according to the method of the present invention, the generation of air bubbles and complicated movement of cell media and cells were not observed either. Unlike the cuvette, the long, thin and hollow specimen-stuffing member restricts the current direction due to its geometrical structure, an even electric field is formed on the entire specimen-stuffing member. The uniform environment in the said specimen-stuffing member enhances the material absorption rate in the cells.

INDUSTRIAL APPLICABILITY

As earlier mentioned, cells can be easily electroporated using the electroporation apparatus according to the present invention. Furthermore, because the cells are electroporated in a capillary, pipe including tubing or micro channel, the electroporated cells can be effectively retrieved and used. The thin, long and hollow structured specimen-stuffing member enables the current to flow only through the narrow piping, such that an even electric field can be provided in the specimen-stuffing member compared with the conventional broad and short cuvette. Therefore, it is possible to reduce errors resulting from experimental conditions. The electroporation apparatus according to the present invention has the electrodes and the specimen-stuffing members, which are attachable and detachable therefrom, to allow the eternal use of platinum electrodes of excellent performance, or cheaper disposable electrodes, such that the specimen-stuffing members can be conveniently disposed for one time use. As electrodes of excellent performance are used, the generation of oxygen due to decomposed water or formation of metal ions can be reduced. Furthermore, there is little loss of specimens. In addition, experiments can be conducted with only a small amount of specimens because the small amount of specimens can be filled in and retrieved from the specimen-stuffing member and retrieved by electroporation. Furthermore, by properly controlling the pressure maintaining means, a large amount of specimen can be automatically experimented, and by using a plurality of electroporation apparatuses in parallel, optimum experimental conditions can be easily created, enabling to process several specimens at the same time.

What is claimed is:

1. An electroporation system for applying an electric pulse or electric pulses to a specimen including cells to thereby electroporate cell membranes and infuse foreign materials into the cells, comprising:
   a plurality of hollow specimen-stuffing members of non-conductive material, wherein the plurality of hollow specimen-stuffing members comprises channels of at least two different lengths;
   a substrate, wherein the substrate comprises a pair of wells for each hollow specimen-stuffing member, and wherein the pair of wells for each hollow specimen-stuffing member is connected to both distal ends of the specimen-stuffing member for fluid communication;
   an electric pulse generator; and
   a pair of electrodes for each pair of wells in electrical connection with the electric pulse generator, wherein the pairs of electrodes are configured to be inserted within the pairs of wells and to apply an electric pulse within the plurality of hollow specimen-stuffing members, and wherein the electric pulse has an electric field intensity that is different for channels of different lengths.

2. The electroporation system according to claim 1, wherein the hollow specimen-stuffing member has a ratio (R, $cm^{-1}$) of a longitudinal length (L, cm) to horizontal cross-sectional area (A, $cm^2$) in the range of 50 to 10,000.

3. The electroporation system according to claim 1, wherein the plurality of hollow specimen-stuffing members comprises channels with a length of 1 mm to 10 cm.

4. The electroporation system according to claim 2, wherein the plurality of hollow specimen-stuffing members comprises channels with a length of 1 cm to 5 cm.

5. The electroporation system according to claim 1, wherein the plurality of hollow specimen-stuffing members comprises channels with a height of 2 µm to 2 mm and a width of 10 µm to 10 µmm.

6. The electroporation system according to claim 5, wherein the plurality of hollow specimen-stuffing members comprises channels with a height of 20 µm to 200 µm and a width of 100 µm to 5 mm.

7. The electroporation system according to claim 1, wherein each of the plurality of hollow specimen-stuffing members comprises a channel of a different length from the other hollow specimen-stuffing members.

8. The electroporation system according to claim 1, wherein the plurality of hollow specimen-stuffing members comprises channels of at least two different widths.

9. The electroporation system according to claim 1, wherein one well of each pair of wells is aligned within a row of wells.

10. The electroporation system according to claim 1, wherein a first well of each pair of wells is aligned within a first row of wells, and wherein a second well of each pair of wells is aligned within a second row of wells.

11. The electroporation system of claim 1, additionally comprising:
a microscope configured to observe cells within the plurality of hollow specimen-stuffing members.

12. The electroporation system of claim 11, wherein the microscope is a fluorescence microscope configured to observe fluorescence associated with the cells.

13. An electroporation system for applying an electric pulse or electric pulses to a specimen including cells to thereby electroporate cell membranes and infuse foreign materials into the cells, comprising:

a plurality of hollow specimen-stuffing members of non-conductive material, wherein the plurality of hollow specimen-stuffing members comprises channels of at least two different lengths;
a substrate, wherein the substrate comprises a pair of wells, and wherein the pair of wells is connected to both distal ends of at least two hollow specimen-stuffing members for fluid communication;
an electric pulse generator; and
a pair of electrodes in electrical connection with the electric pulse generator, wherein the pair of electrodes is configured for insertion within the pair of wells to apply an electric pulse within the plurality of hollow specimen-stuffing members, and wherein the electric pulse has an electric field intensity that is different for channels of different length.

14. The electroporation system according to claim 13, wherein more than two hollow specimen-stuffing members are connected to the pair of wells.

15. The electroporation system according to claim 14, wherein three hollow specimen-stuffing members are connected to the pair of wells.

16. The electroporation system according to claim 14, wherein five hollow specimen-stuffing members are connected to the pair of wells.

17. The electroporation system according to claim 13, wherein each of the plurality of hollow specimen-stuffing members comprises a channel of a different length from the other hollow specimen-stuffing members.

18. The electroporation system according to claim 13, wherein the plurality of hollow specimen-stuffing members comprises channels of at least two different widths.

19. The electroporation system according to claim 13, wherein the plurality of hollow specimen-stuffing members comprises channels with a height of 20 µm to 200 µm and a width of 100 µm to 5 mm.

20. The electroporation system according to claim 13, wherein the hollow specimen-stuffing member has a ratio (R, cm$^{-1}$) of a longitudinal length (L, cm) to horizontal cross-sectional area (A, cm$^2$) in the range of 50 to 10,000.

* * * * *